(12) United States Patent
Sevillano et al.

(10) Patent No.: US 10,239,954 B2
(45) Date of Patent: *Mar. 26, 2019

(54) ANTIBODIES SPECIFIC FOR UROKINASE-TYPE PLASMINOGEN ACTIVATOR AND METHODS OF USE THEREOF FOR TREATING CANCER

(71) Applicants: The Regents of the University of California, Oakland, CA (US); CytomX Therapeutics, Inc., South San Francisco, CA (US)

(72) Inventors: Natalia Sevillano, San Francisco, CA (US); Aaron M. Lebeau, San Francisco, CA (US); Daniel Robert Hostetter, Palo Alto, CA (US); Charles S. Craik, San Francisco, CA (US)

(73) Assignees: THE REGENTS OF THE UNIVERSITY OF CALIFORNIA, Oakland, CA (US); CYTOMX THERAPEUTICS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/608,729

(22) Filed: May 30, 2017

(65) Prior Publication Data
US 2017/0335012 A1  Nov. 23, 2017

Related U.S. Application Data

(63) Continuation of application No. 14/972,631, filed on Dec. 17, 2015, now Pat. No. 9,695,249, which is a continuation of application No. 14/162,439, filed on Jan. 23, 2014, now Pat. No. 9,255,155.

(60) Provisional application No. 61/759,321, filed on Jan. 31, 2013.

(51) Int. Cl.
*A61K 49/00* (2006.01)
*A61K 51/10* (2006.01)
*C07K 16/40* (2006.01)

(52) U.S. Cl.
CPC .......... *C07K 16/40* (2013.01); *A61K 49/0032* (2013.01); *A61K 49/0058* (2013.01); *A61K 51/1075* (2013.01); *C07K 2317/33* (2013.01); *C07K 2317/55* (2013.01); *C07K 2317/565* (2013.01); *C07K 2317/76* (2013.01); *C07K 2317/92* (2013.01)

(58) Field of Classification Search
CPC .......... C07K 16/40; C07K 2317/33; C07K 2317/55; C07K 2317/565; C07K 2317/76; C07K 2317/92; A61K 49/0032; A61K 49/0058; A61K 51/1075
See application file for complete search history.

(56) References Cited

U.S. PATENT DOCUMENTS

| | | |
|---|---|---|
| 7,329,737 B2 | 2/2008 | Sexton et al. |
| 2003/0027981 A1 | 2/2003 | Dano et al. |
| 2003/0050251 A1 | 3/2003 | Semple et al. |
| 2003/0092752 A1 | 5/2003 | Lin et al. |
| 2003/0166514 A1 | 9/2003 | Jones et al. |
| 2006/0024300 A1 | 2/2006 | Adams et al. |
| 2006/0171884 A1 | 8/2006 | Foltz et al. |
| 2006/0246071 A1 | 11/2006 | Green et al. |
| 2008/0025913 A1 | 1/2008 | Bowdish et al. |
| 2008/0051559 A1 | 2/2008 | Craik et al. |
| 2008/0226630 A1 | 9/2008 | Lanetto et al. |
| 2009/0181017 A1 | 7/2009 | Haas et al. |
| 2010/0260762 A1 | 10/2010 | Moe et al. |

FOREIGN PATENT DOCUMENTS

| | | |
|---|---|---|
| WO | WO20010029056 | 4/2001 |
| WO | WO2004003183 | 1/2004 |

(Continued)

OTHER PUBLICATIONS

Paul, WE. Fundamental Immunology, 3rd ed. Raven Press, NY, Chap. 9, pp. 292-295, 1993.*

(Continued)

*Primary Examiner* — Robert S Landsman
(74) *Attorney, Agent, or Firm* — Carol L. Francis; Bozicevic, Field & Francis LLP

(57) ABSTRACT

The present disclosure relates to antibodies specific for urokinase-type plasminogen activator (uPA). According to certain embodiments, the anti-uPA antibody specifically binds to the active form of uPA. In certain aspects, the anti-uPA antibody that specifically binds to active uPA binds specifically to the active form of human uPA (e.g., the antibody does not cross-react with active forms of uPA from non-human organisms). In certain aspects, an anti-uPA antibody of the present disclosure competes for specific binding to uPA with plasminogen activator inhibitor type 1 (PAI-1), where binding of the antibody to uPA results in internalization of a complex that includes the antibody, uPA, and urokinase-type plasminogen activator receptor (uPAR). Also provided are antibodies that specifically bind to uPA and compete for binding to uPA with a synthetic ligand of uPA. The disclosure also provides anti-uPA antibody conjugates and compositions (e.g., pharmaceutical formulations) comprising the antibodies and/or conjugates. Methods and kits related to the anti-uPA antibodies, conjugates, or formulations including the antibodies and/or conjugates are also provided.

22 Claims, 14 Drawing Sheets
Specification includes a Sequence Listing.

(56) References Cited

FOREIGN PATENT DOCUMENTS

| WO | WO2006050177 | 5/2006 |
|---|---|---|
| WO | WO2007075921 | 5/2007 |

OTHER PUBLICATIONS

Rudikoff S. et al. Proc. Natl. Acad. Sci. USA, 79:1979-1983, 1982.*
Colman, PM. Research in Immunology, Elsevier, NY, 145(1):33-36, 1994.*
Abcam—product overview "Anti-uPA antibody [U-16] (ab131433)" URL: http://www.abcam.com/uPA-antibody-U-16-ab131433.html, (2013) 2 pages.
Ahmad et al.,"Inactivation of uPA and its receptor uPAR by 3, 3'-Diindolylmethane (DIM) leads inhibition of Prostate Cancer Cell growth and migration" (2009) J. Cell. Biochem, 107(3):516-27.
Anderson and Piwnica-Worms "AACR/SNMMI State-of-the-Art Molecular Imaging in Cancer Biology and Therapy: Abstracts." (2013) J. Nuclear Medicine, 54(Suppl 1):3A-35.
Bhatt et al. "Quantitation of membrane type serine protease 1 (MT-SP1) in transformed and normal cells" Biol Chem 2003, 384(2):257-266.
Blouse et al. "A Novel Mode of Intervention with Serine Protease Activity" (2009) J. Biol Chem, 284(7):4647-4657.
Botkjaer et al. "Targeting the autolysis loop of urokinase-type plasminogen activator with conformation-specific monoclonal antibodies" (2011) J. Biol Chem, 438:39-51.
Collaborative Computational Project, No. 4 "The CCP4 suite: programs for protein crystallography" Acta Crystallogr D Biol Crystallogr 1994, 50(Pt. 5):760-763.
Copeland, et al. Uniprot ID A3DAI5, Mar. 20, 2007, http://www.uniprot.org/uniprot.org/uniprot/A3DAI5.
Dass et al. "Evolving role of uPA/uPAR system in human cancers" (2008) Cancer Treat Rev, 34(2): 122-136.
De Haard et al. "A large non-immunized human Fab fragment phage library that permits rapid isolation and kinetic analysis of high affinity antibodies" J Biol Chem 1999, 274(26):18218-18230.
Declerck et al. "A Monoclonal Antibody Specific for Two-Chain Urokinase-Type Plasminogen Activator. Application to the Study of the Mechanism of Clot Lysis With Single-Chain Urokinase-Type Plasminogen Activator in Plasma" (1990) Blood, 75(9):1794-800.
Duriseti et al. "Antagonistic Anti-urokinase Plasminogen Activator Receptor (uPAR) Antibodies Significantly Inhibit uPAR-mediated Cellular Signaling and Migration," (2010) J. Biol Chem, 285(35):26878-26888.
Evrard GX et al. "Assessment of automatic ligand building in ARP/wARP" Acta Crystallogr D Biol Crystallogr 2007, 63(Pt. 1):108-117.
Farady et al. "Structure of an Fab-protease complex reveals a highly specific non-canonical mechanism of inhibition" J Mol Biol 2008, 380(2):351-360.
Farady et al. "The mechanism of inhibition of antibody-based inhibitors of membrane-type serine protease 1 (MT-SP1)" J Mol Biol 2007, 369(4):1041-1051.
Foltz et al. American Society of Hematology Annual Meeting Abstracts 2005, 106: Abstract 4816.
GenWay Biotech, Inc.—Product overview "UPA [SPM457], Antibody" (2013), 3 pages.
Harvey et al. "Evaluation of Urinary Plasminogen Activator, Its Receptor, Matrix Metalloproteinase-9, and von Willebrand Factor in Pancreatic Cancer" (2003) Clinical Cancer Res, 9:4935-4943.
Katz et al. "Engineering inhibitors highly selective for the S1 sites of Ser190 trypsin-like serine protease drug targets" (2001) Chemistry and Biology, 8:1107-1121.
Ke et al. "Distinguishing the specificities of closely related proteases" (1997) J. Biol Chem, 272(26):16603-16609.
Knappik et al. (2000) "Fully Synthetic Human Combinatorial Antibody Libraries (HuCAL) Based on Modular Consensus Frameworks and CDRs Randomized with Trinucleotides" J Mol Biol 296(1):57-86.
Kobayashi et al. "Inhibition of in Vitro Ovarian Cancer Cell Invasion by Modulation of Urokinasetype Plasminogen Activator and Cathepsin B" (1992) Cancer Res, 52:3610-3614.
Krissinel & Henrick "Inference of macromolecular assemblies from crystalline state" J Mol Biol 2007, 372(3): 774-97.
Krowarsch et al. "Interscaffolding additivity: binding of P1 variants of bovine pancreatic trypsin inhibitor to four serine proteases" J Mol Biol 1999, 289(1):175-86.
Lebeau et al. "Targeting uPAR with Antagonistic Recombinaht Human Antibodies in Aggressive Breast Cancer," (2013) Cancer Res, 73:2070-2081.
Lee et al. "Activation of Hepatocyte Growth Factor and Urokinase/Plasminogen Activator by Matriptase, an Epithelial Membrane Serine Protease" J. Biol Chem, 2000, 275(47):36720-36725.
Lin et al. "Structural basis for recognition of urokinase-type plasminogen activator by plasminogen activator inhibitor-1" (2011) J. Biol. Chem, 286(9):7027-7032.
List et al. "Matriptase: Potent Proteolysis on the Cell Surface" Mol Med, 2006 12(1-3):1-7.
Liu et al. "The inhibitory effect of HKa in endothelial cell tube formation is mediated by disrupting the uPA-uPAR complex and inhibiting its signaling and internalization." (2008) Am. J. Physiology—Cell Physiology, 295:C257-C267.
Lovell et al. "Structure validation by Cα geometry: φ,ψ and Cβ deviation" Proteins 2003, 50(3):437-450.
McGrath et al. "The sequence and reactive site of ecotin. A general inhibitor of pancreatic serine proteases from Escherichia coli" J Biol Chem 1991, 266(10):6620-6625.
Murshudov et al. "Efficient anisotropic refinement of macromolecular structures using FFT" Acta Crystallogr D Biol Crystallogr 1999, 55(Pt. 1):247-255.
Nelson et al. "Epigenetic alterations in human prostate cancers" (2009) Endocrinology, 150:3991-4002.
Ossowski et al. "Inhibition of urokinase-type plasminogen activator by antibodies: the effect on dissemination of a human tumor in the nude mouse." (1991) Cancer Res, 51:274-281.
Ozawa et al. "The reactive site of trypsin inhibitors" J Biol Chem 1966, 241(17):3955-3961.
Pakneshan et al. "Hypomethylation of urokinase (uPA) promoter in breast and prostate cancer: prognostic and therapeutic implications" (2005) Curr Cancer Drug Targets, 5:471-488.
Pakneshan et al. "Methylation status of uPA promoter as a molecular mechanism regulating prostate cancer invasion and growth in vitro and in vivo" (2003) FASEB J, 17:1081-1088.
Perona and Craik "Evolutionary Divergence of Substrate Specificity within the Chymotrypsin-like Serine Protease Fold" (1997) J. Biol. Chem, 272(48):29987-29990.
Petersen et al. "Localization of epitopes for monoclonal antibodies to urokinase-type plasminogen activator Relationship between epitope localization and effects of antibodies on molecular interactions of the enzyme" (2001) Eur. J. Biochem., 268:4430-4439.
Pittman et al. "Neuronal Plasminogen Activators: Cell Surface Binding Sites and Involvement in Neurite Outgrowth" (1989) J. Neuroscience, 9(12):4269-4286.
Read "Pushing the boundaries of molecular replacement with maximum likelihood" Acta Crystallogr D Biol Crystallogr 2001, 57(Pt. 10):1373-1382.
Schneider et al. "A reverse binding motif that contributes to specific protease inhibition by antibodies" (2012) J. Mol Biol, 415:699-715.
Sgier et al. "Isolation and characterization of an inhibitory human monoclonal antibody specific to the urokinase-type plasminogen activator, uPA" (2010) Protein Eng Des Sel, 23:261-269.
Shukeir et al. "Alteration of the methylation status of tumor-promoting genes decreases prostate cancer cell invasiveness and turmorigenesis in vitro and in vivo" (2006) Cancer Res, 66:9202-9210.
Sperl et al. "(4-Aminomethyl)phenylguanidine derivatives as nonpeptidic highly selective inhibitors of human urokinase" (2000) PNAS, 97(10):511.-5118.
Spraggon et al. "The crystal structure of the catalytic domain of human urokinase-type plasminogen activator" (1995) Structure, 3:681-691.

(56) References Cited

OTHER PUBLICATIONS

Stewart et al. "The relevance of a hypoxic tumour microenvironment in prostate cancer" (2010) *BJU Int*, 105:8-13.
Sun et al. "Potent and selective inhibition of membrane-type serine protease 1 by human single-chain antibodies" *Biochemistry* 2003, 42(4):892-900.
Takeuchi et al. "Cellular Localization of Membrane-type Serine Protease 1 and Identification of Protease-activated Receptor-2 and Single-chain Urokinase-type Plasminogen Activator as Substrates" *J. Biol Chem.*, (2000) 275(34):26333-26342.
Takeuchi et al. "Reverse biochemistry: use of macromolecular protease inhibitors to dissect complex biological processes and identify a membrane-type serine protease in epithelial cancer and normal tissue" *Proc Natl Acad Sci USA* 1999, 96(20):11054-11061.
Thermo Scientific—Product data sheet "Urokinase Plasminogen Activator Monoclonal Antibody (SPM457)" (Date not available) 1 page.
Uhland "Matriptase and its putative role in cancer" *Cell. Mol. Life Sci.* 2006, 63(24):2968-2978.
Ulisse et al. "The urokinase plasminogen activator system: A target for anti-cancer therapy" (2009) *Curr. Cancer Drug Targets*, 9:32-71.
Ulmert et al. "Imaging Androgen Receptor Signaling with a Radiotracer Targeting Free Prostate-Specific Antigen" (2012) *Cancer Discov*, 2:320-327.
Usher et al. "Expression of urokinase plasminogen activator, its receptor and type-1 inhibitor in malignant and benign prostate tissue" (2005) *Int J Cancer*, 113:870-880.
Wu et al. "Length distribution of CDRH3 in antibodies" *Proteins* 1993, 16(1):1-7.
Yamamoto et al. "Expression and Localization of Urokinase-Type Plasminogen Activator in Human Astrocytomas in Vivo" (1994) *Cancer Res*, 54:3556-3661.
Zemlin et al. "Expressed murine and human CDR-H3 intervals of equal length exhibit distinct repertoires that differ in their amino acid composition and predicted range of structures" *J Mol Biol* 2003, 334(4):733-749.
Zeslawska et al. "Crystals of the Urokinase Type Plasminogen Activator Variant bc-uPA in Complex with Small Molecule Inhibitors Open the Way towards Structure-based Drug Design" (2000) *J. Mol Biol*, 301:465-475.

\* cited by examiner

FIG. 4
A
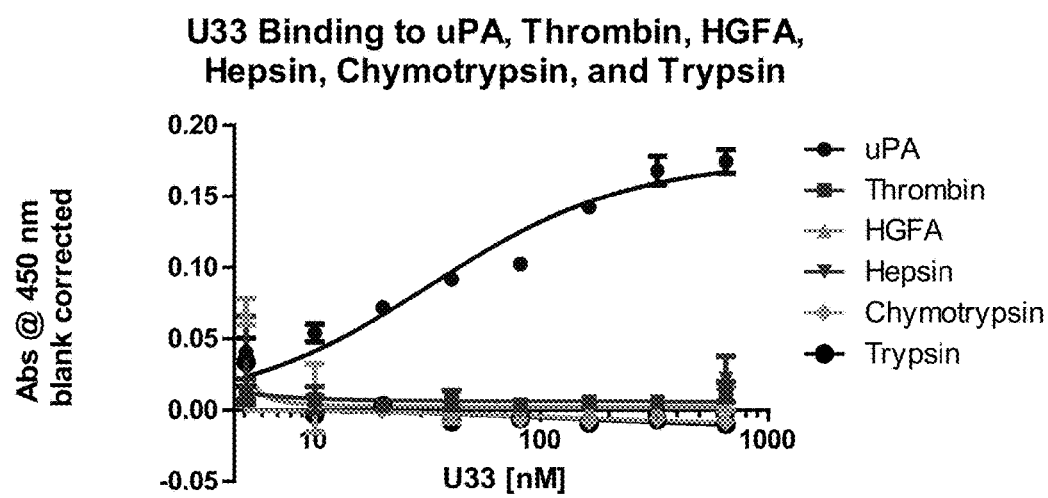
B
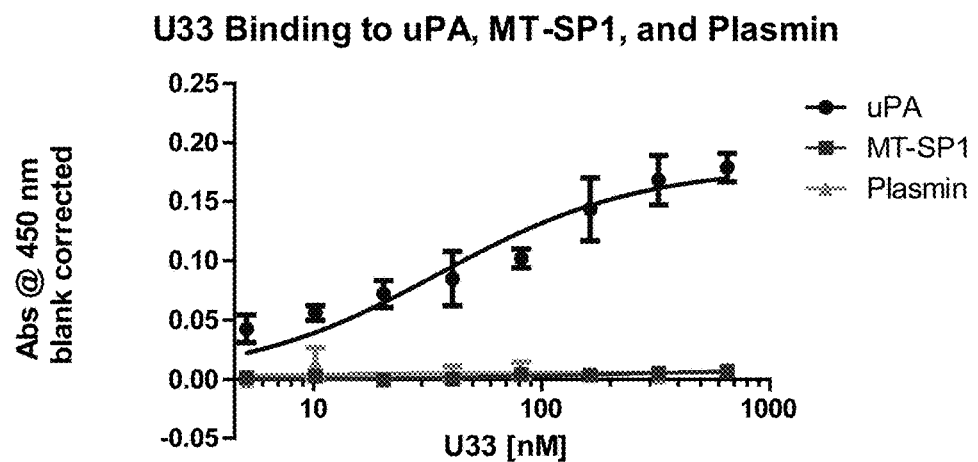

FIG. 4 (cont'd)
C
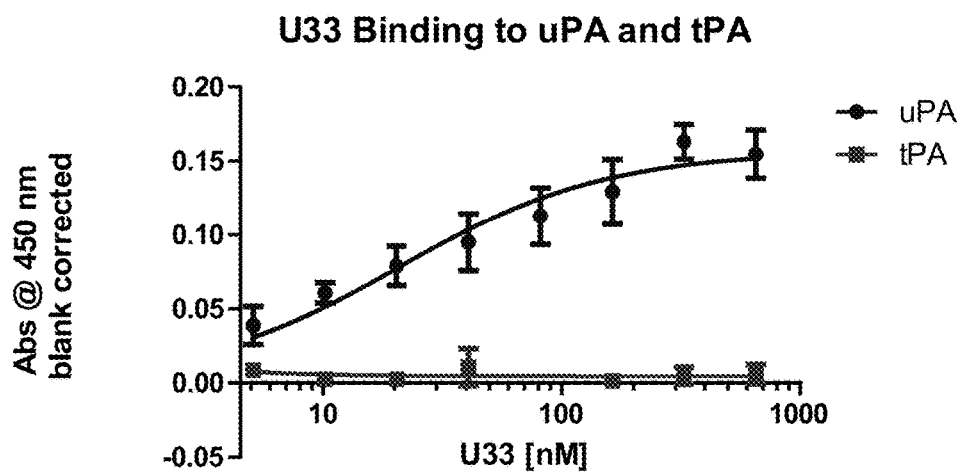
D
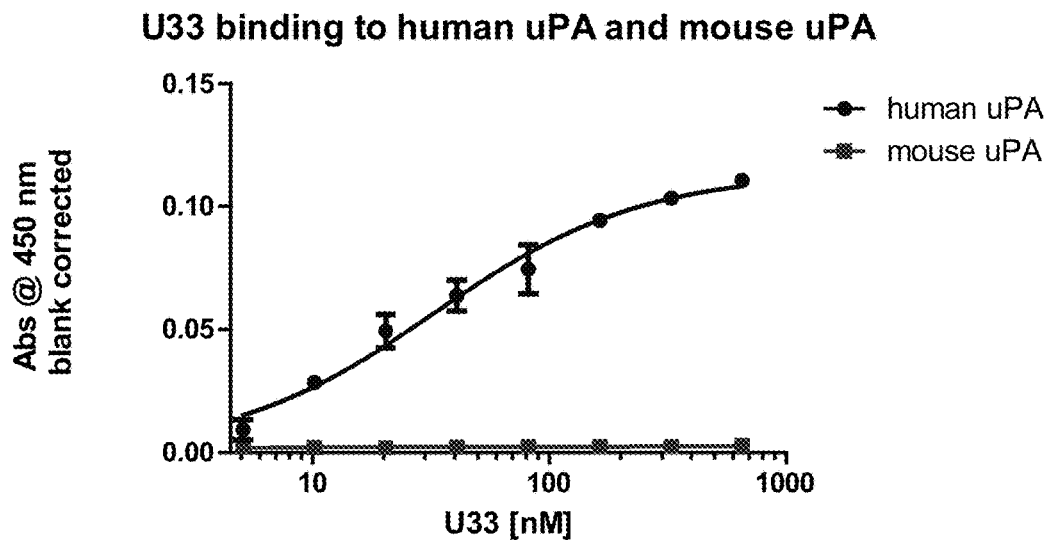

FIG. 5
A
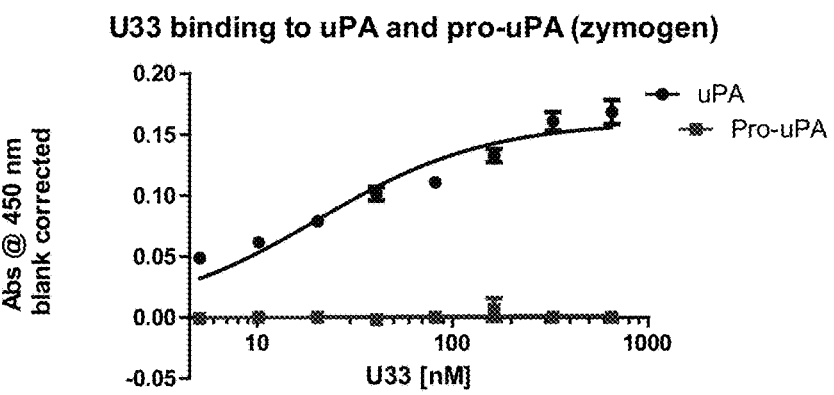
B
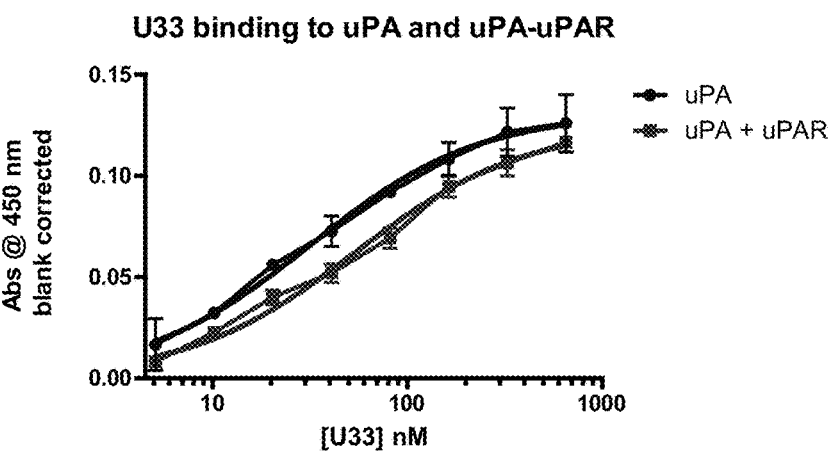
C
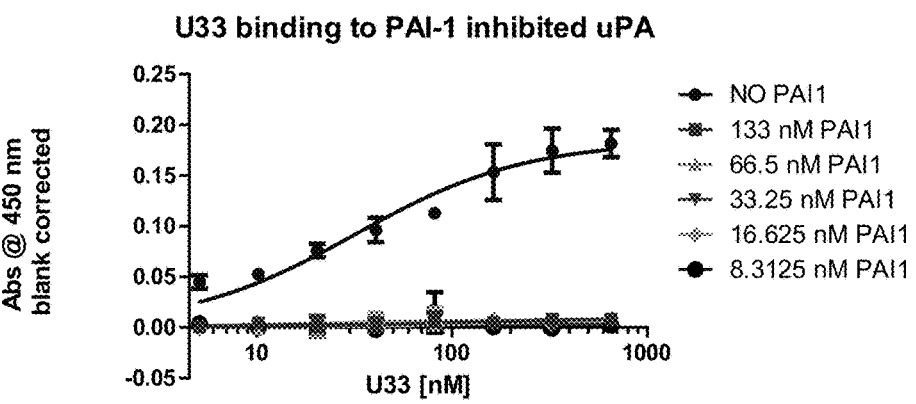

FIG. 6
A
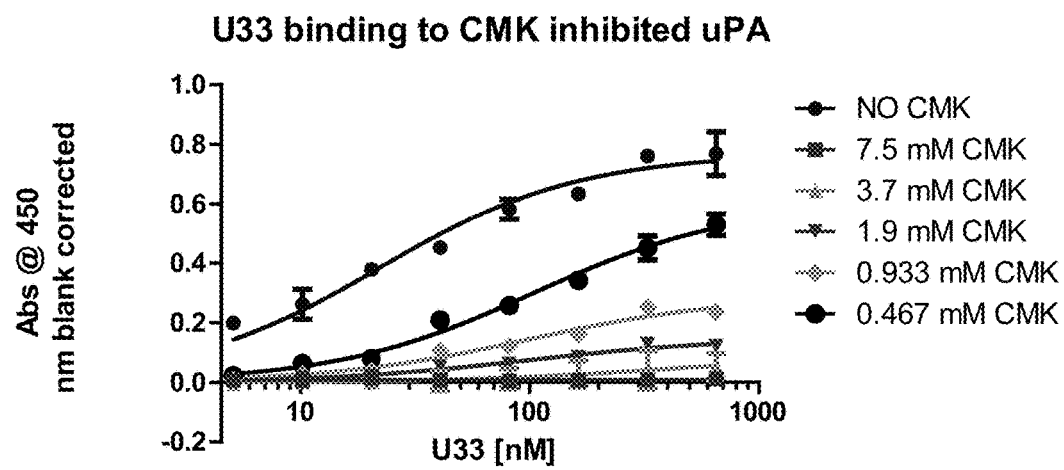
B
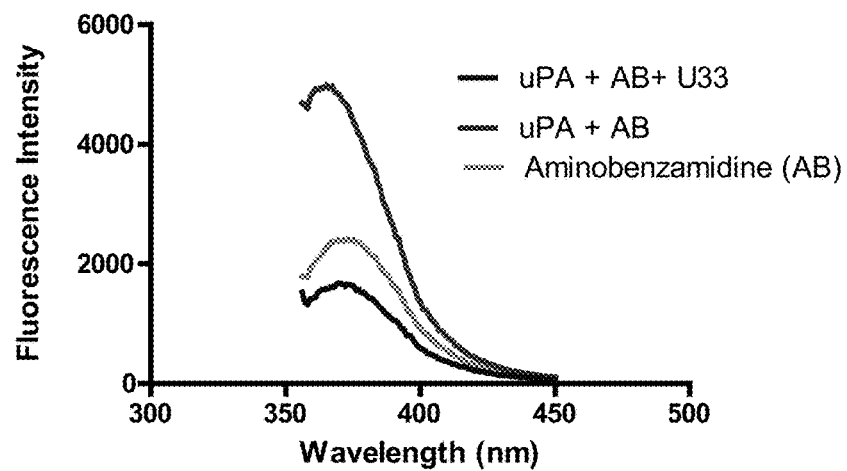

Light chain
EIVLTQSPLSLPVTPGEPASISCRSSQTLMNRNGNNFLDWYLQKPGQSPQLLIYLGSNRAPGVPDRFSGS
GSGTDFTLKISRVEAEDVGVYYCMQRIEFPYTFGQGTKLEIKRTVVAPSVFIFPPSDEQLKSGTASVVCL
LNNFYPREAKVQWKVDNALQSGNSQESVTEQDSKDSTYSLSSTLTLSKADYEKHKVYACEVTHQGLSSPV
TKSFNRGEC

Heavy chain
EVQLVQSGGGLVKPGRSLRLSCTASGFTFGDYAMSWVRQAPGKGLEWVGFIRSKAYGGTTEYAAVKGRFT
ISRDDSKSIAYLQMNSLKTEDTAVYYCIRGANWNWGQGTLVTVSSASTKGPSVFPLAPSSKSTSGGTAAL
GCLVKDYFPEPVTVSWNSGALTSGVHTFPAVLQSSGLYSLSSVVTVPSSSLGTQTYICNVNHKPSNTKVD
KKVEPKSCAAAHHHHHHGAAEQKLISEEDLNGAA CDRs:

| CDRL1 | CDRL2 | CDRL3 |
|---|---|---|
| RSSQTLMNRNGNNFLD | LGSNRAP | MQRIEFPYT |

| CDRH1 | CDRH2 | CDRH3 |
|---|---|---|
| GFTFGDYAMS | FIRSKAYGGTTE | IRGANWN |

B

Light chain
GAAATTGTGCTGACTCAGTCTCCACTCTCCCTGCCCGTCACCCCTGGAGAGCCGGCCTCCATCTCCTGCA
GGTCTAGTCAGAGCCTCATGAATAGAAATGGAAACAACTTTTTGGATTGGTACCTGCAGAAGCCAGGGCA
GTCTCCACAGCTCCTGATCTACTTGGGTTCTAATCGGCCCCGGGGTCCCTGACAGGTTCAGTGGCAGT
GGATCAGGCACAGATTTTACACTGAAAATCAGCAGAGTGGAGGCTGAGGATGTTGGGGTTTATTACTGCA
TGCAACGTATAGAGTTTCCGTACACTTTTGGCCAGGGGACCAAGCTGGAGATCAAACGAACTGTGGTTGC
ACCATCTGTCTTCATCTTCCCGCCATCTGATGAGCAGTTGAAATCTGGAACTGCCTCTGTTGTGTGCCTG
CTGAATAACTTCTATCCCAGAGAGGCTAAAGTACAGTGGAAGGTGGATAACGCCCTCCAATCGGGTAACT
CCCAGGAGAGTGTCACAGAGCAGGACAGCAAGGACAGCACCTACAGCCTCAGCAGCACCCTGACGCTGAG
CAAAGCAGACTACGAGAAACACAAAGTCTACGCCTGCGAAGTCACCCATCAGGGCCTGAGCTCGCCCGTC
ACAAAGAGCTTCAACAGGGGAGAGTGTTAATAA

Heavy chain
GAGGTCCAGCTGGTACAGTCTGGGGGAGGCTTGGTAAAGCCAGGGCGGTCCCTGAGACTCTCCTGTACAG
CTTCTGGATTCACCTTTGGTGATTATGCTATGAGCTGGGTCCGCCAGGCTCCAGGGAAGGGGCTGGAGTG
GGTAGGTTTCATTAGAAGCAAAGCTTATGGTGGGACAACAGAATACGCCGCGTCTGTGAAAGGCAGATTC
ACCATCTCAAGAGATGATTCCAAAAGCATCGCCTATCTGCAAATGAACAGCCTGAAAACCGAGGACACAG
CCGTGTATTACTGTATCAGAGGTGCAAACTGGAACTGGGGCCAGGGCACCCTGGTCACCGTCTCAAGCGC
CTCCACCAAGGGCCCATCGGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAACTCAGGCGCCCTGACCA
GCGGCGTCCACACCTTCCCGGCTGTCCTACAGTCCTCAGGACTCTACTCCCTCAGCAGCGTAGTGACCGT
GCCCTCCAGCAGCTTGGGCACCCAGACCTACATCTGCAACGTGAATCACAAGCCCAGCAACACCAAGGTG
GACAAGAAAGTTGAGCCCAAATCTTGTGCGGCCGCACATCATCATCACCATCACGGGGCCGCAGAACA
AAAACTCATCTCAGAAGAGGATCTGAATGGGGCCGCATAG

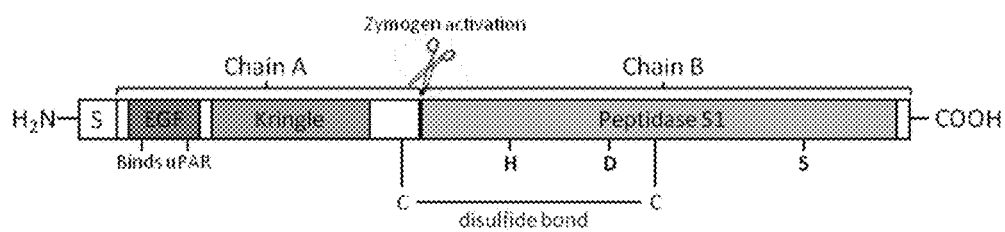

B

```
1         10        20        30        40        50        60
MRALLARLLLCVLVVSDSKGSNELHQVPSNCDCLNGGTCVSNKYFSNIHWCNCPKKFGGQ 61        70        80        90        100       110       120
HCEIDKSKTCYEGNGHFYRGKASTDTMGRPCLPWNSATVLQQTYHAHRSDALQLGLGKHN 121       130       140       150       160       170       180
YCRNPDNRRRPWCYVQVGLKPLVQECMVHDCADGKKPSSPPEELKFQCGQKTLRPRFKI 181       190       200       210       220       230       240
QGEFTTIENQPWFAAIYRRHRGGSVTYVCGGSLISPCWVISATHCFIDYPKKEDYIVYLG 241       250       260       270       280       290       300
RSRLNSNTQGEMKFEVENLILHKDYSADTLAHHNDIALLKIRSKEGRCAQPSRTIQTIC 301       310       320       330       340       350       360
PSMYNDPQFGTSCEITGFGKENSTDYLYPEQLKMTVVKLISHRECQQPHYYGSEVTTKML 361       370       380       390       400       410       420
CAADPQWKTDSCQGDSGGPLVCSLQGRMTLPGIVSWGRGCALKDKPGVYTRVSHFLPWIR 421       430
SHTKEENGLAL
```

ANTIBODIES SPECIFIC FOR UROKINASE-TYPE PLASMINOGEN ACTIVATOR AND METHODS OF USE THEREOF FOR TREATING CANCER

CROSS-REFERENCE TO RELATED APPLICATIONS

This application is a continuation of U.S. application Ser. No. 14/972,631, filed Dec. 17, 2015, now issued as U.S. Pat. No. 9,695,249 on Jul. 4, 2017, which application is a continuation of U.S. application Ser. No. 14/162,439, filed Jan. 23, 2014 now U.S. Pat. No. 9,255,155, issued Feb. 9, 2016, which application claims priority benefit of U.S. provisional application Ser. No. 61/759,321, filed Jan. 31, 2013, which application is incorporated herein by reference in its entirety.

INTRODUCTION

Certain diseases have been found to be dependent upon misregulated enzyme function, including proteases. In particular, proteases have been implicated in a number of functions essential for cancer progression. These include extracellular matrix remodeling, release of cytokines, and loss of apoptotic response. One particular protease that has been implicated in cancer progression is the serine protease urokinase type plasminogen activator (uPA) (Ahmad et al. (2009) J. Cell. Biochem 107(3):516-27; Ulisse et al. (2009) Curr. Cancer Drug Targets 9:32-71). Single chain pro-uPA is secreted as a 411 amino acid zymogen and becomes activated by plasmin cleavage of the K158-I159 peptide bridge, thus generating uPA, a two-chain molecule held together by a single disulfide bond at C148-C279. A further cleavage releases an amino terminal domain that includes an "EGF-like" and a "kringle" domain. The remaining carboxyterminal region (low molecular weight uPA) retains full catalytic activity. Active uPA activates plasminogen to plasmin, a broad spectrum serine protease. When uPA is bound to uPAR, the uPA-uPAR complex is not internalized and remains on the cell surface. When receptor-bound uPA is bound by the specific plasminogen activator inhibitor type 1 (PAI-1), the resulting PAI-1-uPA-uPAR complex is internalized. Upon internalization, uPA and PAI-1 are degraded in the lysosomes, while uPAR is recycled back to the cell surface.

SUMMARY

The present disclosure relates to antibodies specific for urokinase-type plasminogen activator (uPA). According to certain embodiments, the anti-uPA antibody specifically binds to the active form of uPA. In certain aspects, the anti-uPA antibody that specifically binds to active uPA binds specifically to the active form of human uPA (e.g., the antibody does not cross-react with active forms of uPA from non-human organisms). In certain aspects, an anti-uPA antibody of the present disclosure competes for specific binding to uPA with plasminogen activator inhibitor type 1 (PAI-1), where binding of the antibody to uPA results in internalization of a complex that includes the antibody, uPA, and urokinase-type plasminogen activator receptor (uPAR). Also provided are antibodies that specifically bind to uPA and compete for binding to uPA with a synthetic ligand of uPA. The disclosure also provides anti-uPA antibody conjugates and compositions (e.g., pharmaceutical formulations) comprising the antibodies and/or conjugates. Methods and kits related to the anti-uPA antibodies, conjugates, or formulations including the antibodies and/or conjugates are also provided.

Accordingly, the present disclosure provides antibodies that specifically bind to urokinase-type plasminogen activator (uPA). The antibodies may be non-human antibodies (e.g., mouse antibodies, rabbit antibodies, or any non-human antibody), humanized antibodies, or fully human antibodies (e.g., a fully human recombinant antibody identified from a phage display library, or the like). Antibodies of the present disclosure bind to one or more epitopes of uPA. According to certain embodiments, the antibody binds to the heavy (B) chain of uPA. Such an antibody may bind to the serine protease domain (SPD) of uPA. An antibody that binds to the SPD of uPA may bind to the active site of uPA, or may bind to a region outside of the active site. In certain aspects, the anti-uPA antibody does not bind to the autolysis loop of uPA. According to certain embodiments, the anti-uPA antibody does not bind to the activation domain of uPA. In certain aspects, the antibody specifically binds to urokinase-type plasminogen activator (uPA) and competes for binding to uPA with a ligand of uPA, e.g., a synthetic ligand of uPA. In certain aspects, the antibody competes for binding to uPA with a uPA ligand, which ligand binds to the active site of uPA without binding to an exosite of uPA (e.g., the ligand binds to the active site of uPA independent of interactions with an exosite (e.g., a region outside of the active site) of uPA).

The antibodies provided by the present disclosure may include one or more (e.g., 1, 2, 3, 4, 5, or all 6) complementary determining regions (CDRs) set forth in Table 1, FIG. 11 and SEQ ID NOs:1-6, or conservative variants of one or more such CDRs.

According to certain embodiments, an antibody of the present disclosure competes for specific binding to uPA with plasminogen activator inhibitor type 1 (PAI-1). Binding of the antibody to uPA results in internalization of a complex that includes the antibody, uPA, and urokinase-type plasminogen activator receptor (uPAR). In certain aspects, the complex does not include PAI-1.

In certain aspects, provided is an isolated antibody that specifically binds to uPA (e.g., specifically binds to the active form of uPA (e.g., two-chain high molecular weight uPA and/or two-chain low molecular weight uPA)), where the antibody competes for binding to uPA with a synthetic ligand (e.g., a small molecule such as p-aminobenzamidine, a synthetic peptide ligand, and the like) of uPA. According to certain embodiments, the substrate is a synthetic peptide ligand, which ligand is EGR-CMK (Glu-Gly-Arg-CMK). In other aspects, the ligand is the synthetic peptide ligand S-2444 (H-D-Glu-Gly-Arg-p-nitroanilide).

Any antibody described above may be an antibody that competes for specific binding to uPA with an antibody that includes: a heavy chain complementary determining region 1 (HCDR1) having the amino acid sequence of SEQ ID NO:1; a heavy chain complementary determining region 2 (HCDR2) having the amino acid sequence of SEQ ID NO:2; a heavy chain complementary determining region 3 (HCDR3) having the amino acid sequence of SEQ ID NO:3; a light chain complementary determining region 1 (LCDR1) having the amino acid sequence of SEQ ID NO:4; a light chain complementary determining region 2 (LCDR2) having the amino acid sequence of SEQ ID NO:5; and a light chain complementary determining region 3 (LCDR3) having the amino acid sequence of SEQ ID NO:6. In certain aspects, such an antibody includes: a heavy chain complementary determining region 1 (HCDR1) having the amino acid sequence of SEQ ID NO:1; a heavy chain complementary determining region 2 (HCDR2) having the amino acid sequence of SEQ ID NO:2; a heavy chain complementary determining region 3 (HCDR3) having the amino acid sequence of SEQ ID NO:3; a light chain complementary determining region 1 (LCDR1) having the amino acid sequence of SEQ ID NO:4; a light chain complementary determining region 2 (LCDR2) having the amino acid sequence of SEQ ID NO:5; and a light chain complementary determining region 3 (LCDR3) having the amino acid sequence of SEQ ID NO:6. Optionally, the antibody includes a heavy chain polypeptide that includes a variable region including the amino acid sequence set forth in SEQ ID NO:7, a light chain polypeptide that includes a variable region including the amino acid sequence set forth in SEQ ID NO:8, or heavy and light chain polypeptides that include variable regions including the amino acid sequences set forth in SEQ ID NO:7 and SEQ ID NO:8, respectively.

Also provided is an isolated antibody that includes: a heavy chain complementary determining region 1 (HCDR1) having the amino acid sequence of SEQ ID NO:1; a heavy chain complementary determining region 2 (HCDR2) having the amino acid sequence of SEQ ID NO:2; a heavy chain complementary determining region 3 (HCDR3) having the amino acid sequence of SEQ ID NO:3; a light chain complementary determining region 1 (LCDR1) having the amino acid sequence of SEQ ID NO:4; a light chain complementary determining region 2 (LCDR2) having the amino acid sequence of SEQ ID NO:5; and a light chain complementary determining region 3 (LCDR3) having the amino acid sequence of SEQ ID NO:6. Optionally, the antibody includes a heavy chain polypeptide that includes a variable region including the amino acid sequence set forth in SEQ ID NO:7, a light chain polypeptide that includes a variable region including the amino acid sequence set forth in SEQ ID NO:8, or heavy and light chain polypeptides that include variable regions including the amino acid sequences set forth in SEQ ID NO:7 and SEQ ID NO:8, respectively.

Any antibody described above may, upon binding to uPA, result in internalization of a complex comprising the antibody, uPA, and urokinase-type plasminogen activator receptor (uPAR). According to certain embodiments, the internalized antibody/uPA/uPAR complex does not include PAI-1.

Any of the antibodies described above may be a "full-length" or "whole" antibody (e.g., a full-length IgG antibody), or may be an antibody fragment. The antibody is an antibody fragment, the fragment may be an Fv, scFv, Fab, F(ab')2, Fab', or any other type of antibody fragment of interest.

Nucleic acids encoding any of the antibodies of the present invention are also provided. For example, the nuceic acid sequences encoding the U33 heavy and light chain variable polypeptides are provided in FIG. 11, panel B. the nucleic acids may be present in an expression vector for production of any antibody of the present disclosure in a cell.

Antibody conjugates are also provided. The conjugates include any antibody of the present disclosure and an agent. The agent may be selected from a therapeutic agent, and a labeling agent, or an agent useful for both therapeutic and labeling purposes. When the conjugate includes a therapeutic agent, the agent may be a cytotoxic agent, such as a radionuclide, a chemotherapeutic agent, a toxin, or any other thereapeutic agent of interest. When the conjugate includes a labeling agent, the agent may be an in vivo imaging agent. Such agents find use in, e.g., the detection, diagnosis and/or prognosis of uPA related diseases (e.g., cancer). Such agents find use in in vivo imaging applications such as near-infrared (NIR) imaging, single photon emission computed tomography (SPECT), and/or the like, for detection, diagnosis and/or prognosis of uPA related diseases (e.g., cancer).

Also provided are sterile pharmaceutical compositions that include any of the antibodies of the present disclosure described herein (or any of the antibody conjugates of the present disclosure described herein), and a pharmaceutically acceptable carrier.

In certain aspects, the present disclosure provides methods of treating uPA-related diseases. For example, according to one embodiment, provided is a method for treating cancer. The method includes the step of administering to a subject in need thereof a therapeutically effective amount of any anti-uPA antibodies of the present disclosure, any anti-uPA antibody conjugate of the present disclosure, or any pharmaceutical composition that includes such an antibody or conjugate. When the treatment method is a method of treating cancer, the cancer may be any cancer in which uPA activity is involved (e.g., by causing cell cycle dysregulation, facilitating metastasis and/or invasiveness of the cancer, and/or the like). In certain aspects, the method is a method for treating a cancer selected from prostate cancer (e.g., castration-resistant prostate cancer), breast cancer, gastric cancer, colorectal cancer, esophageal cancer, renal cancer, endometrial cancer, ovarian cancer, and combinations thereof.

BRIEF DESCRIPTION OF FIGURES

FIG. 4, panel A shows selectivity of U33 binding to uPA compared to thrombin, HGFA, hepsin, chymotrypsin, and trypsin. Panel B shows selectivity of U33 binding to uPA compared to MT-SP1 and plasmin. Panel C shows selectivity of U33 binding to uPA compared to tPA. Panel D shows selectivity of U33 binding to human uPA compared to mouse uPA.

FIG. 5, panel A shows U33 binding to uPA versus pro-uPA (zymogen uPA). Panel B shows U33 binding to uPA versis uPA bound to uPAR. Panel C shows U33 binding to uPA versus uPA inhibited by PAI-1.

FIG. 6, panel A shows U33 binding to uPA versus uPA inhibited by a CMK inhibitory peptide. Panel B shows displacement of p-aminobenzamidine by U33.

FIG. 11, panel A shows the amino acid sequences (Light chain: SEQ ID NO:8; Heavy chain: SEQ ID NO:7) of the U33 light and heavy chain polypeptides, with the CDRs underlined in the sequences and separately presented in the tables shown (CDRL1: SEQ ID NO:4; CDRL2: SEQ ID NO;5; CDRL3: SEQ ID NO:6; CDRH1: SEQ ID NO:1; CDRH2: SEQ ID NO:2; CDRH3: SEQ ID NO:3). CDRS are defined by the Kabat numbering system (Johnson et al. *Nucleic Acids Research*, 2000, 28: 214-218). Panel B shows the nucleic acid sequences (Light chain: SEQ ID NO:9; Heavy chain: SEQ NO:10) that encode the light and heavy chains of the U33 Fab.

FIG. 12, panel A schematically illustrates the different domains and other features of uPA. Here, pro-uPA (or "zymogen" uPA) is depicted before conversion to two-chain active uPA. Panel B shows the amino acid sequence of uPA (SEQ ID NO:11). The B chain is indicated by shading Arrows indicate certain amino acids of interest in the S1 pocket (Asp$^{370}$, Ser$^{371}$ and Gly$^{399}$); the S2 pocket (His$^{272}$); the S3 pocket (Leu$^{270}$ and Ala$^{271}$); and amino acids of interest essential for catalysis (e.g., His$^{224}$, Asp$^{275}$ and/or Ser$^{376}$) Underlined are the cysteines (Cys$^{168}$ and Cys$^{299}$) involved in the disulphide bridge between the A and B chains of two-chain (active) uPA.

DETAILED DESCRIPTION OF EXEMPLARY EMBODIMENTS

Figure 1:
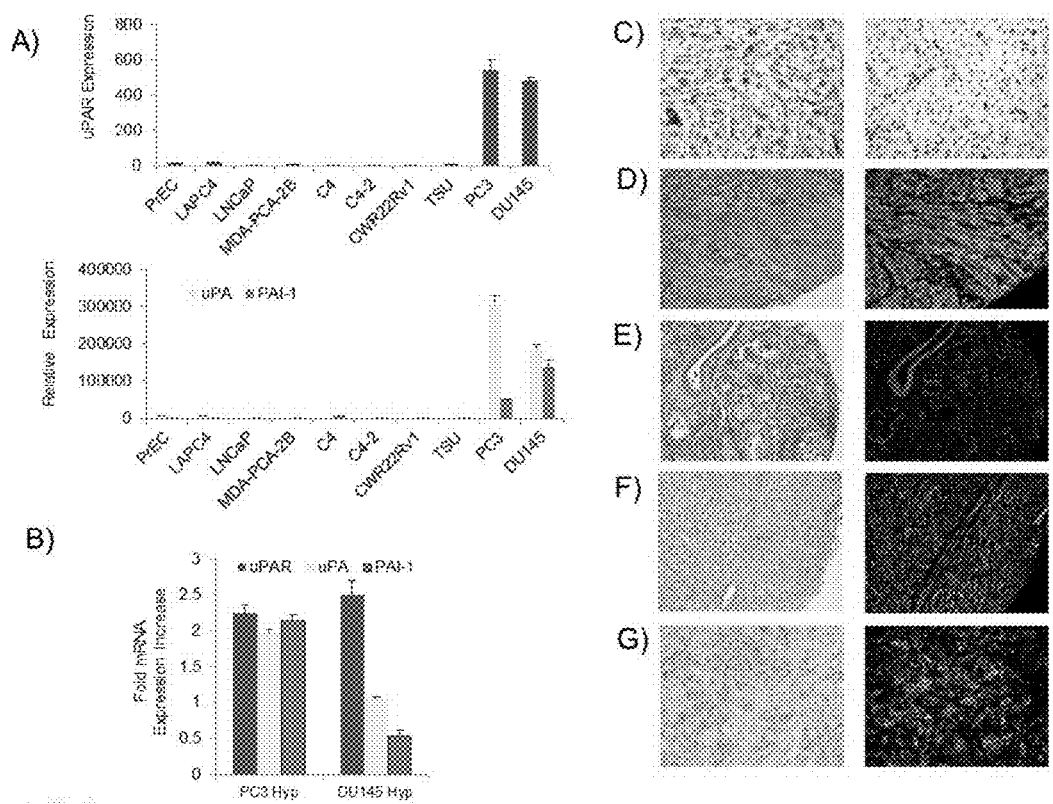
FIG. 1, panels A-G, depict uPA expression in prostate cancer cell lines and prostate cancer tissue microarray sections. Panel A shows mRNA levels of uPAR (top) and uPA and PAI-1 (bottom) analyzed using quantitative RT-PCR in prostate cancer cell lines and normal human prostate epithelial cells. Panel B shows qRT-PCR analysis of the PAS components in PC3 and DU145 cells cultured under 5% $O_2$ for 72 hrs. The increase in mRNA expression is compared to cells grown under normoxia. The left bar, middle bar, and right bar for the PC3 and DU145 cell experiments correspond to uPAR, uPA and PAI-1, respectively. Panel C shows IHC staining of a PC3 xenograft section (left) and a DU145 xenograft section (right) for total uPA protein using the antibody sc-14019. Panels D-G show uPA protein in prostate cancer tissue microarray sections by immunofluoresence. H&E stained sections are viewed on the left with the merged fluoresence channels on the right with uPA (green), E-cadherin (red) and nuclei (DAPI). The sections stained are: adenocarcinoma, grade II, T1N0M0 (2+3=5) (Panel D); adenocarcinoma, grade II, T2N0M0 (1+4=5) (Panel E); adenocarcinoma, grade IV, T3bN1M0 (4+5=9) (Panel F); bone metastasis, grade IV(Panel G).

The present disclosure relates to antibodies specific for urokinase-type plasminogen activator (uPA). According to certain embodiments, the anti-uPA antibody specifically binds to the active form of uPA (e.g., the antibody does not bind to the zymogen form of uPA). In certain aspects, the anti-uPA antibody that specifically binds to active uPA binds specifically to the active form of human uPA (e.g., the antibody does not cross-react with active forms of uPA from non-human organisms). In certain aspects, an anti-uPA antibody of the present disclosure competes for specific binding to uPA with plasminogen activator inhibitor type 1 (PAI-1), where binding of the antibody to uPA results in internalization of a complex that includes the antibody, uPA, and urokinase-type plasminogen activator receptor (uPAR). In certain aspects, this complex does not include PAI-1. Also provided are antibodies that specifically bind to uPA and compete for binding to uPA with a uPA ligand, such as a synthetic peptide ligand (e.g., p-aminobenzamidine, EGR-CMK, S-2444, and the like) of uPA. The disclosure also provides anti-uPA antibody conjugates and compositions (e.g., pharmaceutical formulations) comprising the antibodies and/or conjugates. Methods and kits related to the anti-uPA antibodies, conjugates, or formulations including the antibodies and/or conjugates are also provided.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "an antigen" includes a plurality of such antigens and reference to "the peptide" includes reference to one or more peptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

When describing the antibodies, conjugates, pharmaceutical formulations containing such, and methods of producing and using such antibodies, conjugates, or formulations, the following terms have the following meanings unless otherwise indicated. It should also be understood that any of the moieties defined forth below may be substituted with a variety of substituents, and that the respective definitions are intended to include such substituted moieties within their scope.

The terms "polypeptide" and "protein" are used interchangeably throughout the application and mean at least two covalently attached amino acids, which includes proteins, polypeptides, oligopeptides, peptides, and fragments thereof. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. Normally, the amino acids are in the (S) or L-configuration. If non-naturally occurring side chains are used, non-amino acid substituents may be used, for example to prevent or retard in vivo degradation. Naturally occurring amino acids are normally used and the protein is a cellular protein that is either endogenous or expressed recombinantly. The terms includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 5-50 residues (e.g., 8-20 residues) in length.

As used herein, the term "orientation," refers to the positional relationship of a protease substrate relative the protease to which it is bound. By convention, the orientation of a substrate to its protease is specified from N-terminus to C-terminus based on sites named Pn, . . . , P3, P2, P1, P1', P2', P3', . . . , Pn', where P1-P1' denotes the scissile bond to be cleaved by the protease and n is the number of the feature relative to the scissile bond. Their respective binding sites on the protease are named Sn, . . . , S3, S2, S1, S 2', S3', . . . , Sn' and n is the number of the feature relative to the active site. In accordance with this nomenclature, the scissile bond of a cleavable substrate is presented to the active site in an N-terminus to C-terminus orientation relative to sites S1 and S1'. If the scissile bond of a substrate is presented to the active site in a C-terminus to N-terminus orientation relative to sites S1 and S1', the scissile bond is considered to be in the "reversed orientation."

By "nucleic acid" herein is meant either DNA or RNA, or molecules which contain both deoxy- and ribonucleotides. Nucleic acid may be naturally occurring or synthetically made, and as such, includes analogs of naturally occurring polynucleotides in which one or more nucleotides are modified over naturally occurring nucleotides.

The term "chemotherapy" as used herein refers to use of an agent (e.g., drug, antibody, etc.), particularly an agent(s) that is destructive to a cancerous cell, in treatment of a disease, with treatment of cancer being of particular interest.

A "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell" or "cancerous cell", and encompasses cancer cells of a solid tumor, a semi-solid tumor, a primary tumor, a metastatic tumor, and the like.

The term "conjugated" generally refers to a chemical linkage, either covalent or non-covalent, usually covalent, that proximally associates one molecule of interest with second molecule of interest.

The terms "antigen" and "epitope" are well understood in the art and refer to the portion of a macromolecule (e.g., a polypeptide) which is specifically recognized by a component of the immune system, e.g., an antibody or a T-cell antigen receptor. As used herein, the term "antigen" encompasses antigenic epitopes, e.g., fragments of an antigen which are antigenic epitopes. Epitopes can be recognized by antibodies in solution, e.g. free from other molecules. Epitopes can be recognized by T-cell antigen receptor when the epitope is associated with a class I or class II major histocompatibility complex molecule.

The terms "derivative" and "variant" refer to without limitation any compound or antibody which has a structure or sequence derived from the compounds and antibodies of the present disclosure and whose structure/sequence is sufficiently similar to those disclosed herein and based upon that similarity, would be expected, by one skilled in the art, to exhibit the same or similar activities and utilities as the claimed and/or referenced compounds or antibody.

The term "effective amount" of a composition as provided herein is intended to mean a non-lethal but sufficient amount of the composition to provide the desired utility. For instance, for eliciting a favorable response in a subject to treat a disease (e.g., cancer), the effective amount is the amount which eliminates or diminishes the symptoms associated with the disorder, e.g., so as to provide for control of cancer metastatis, to eliminate cancer cells, and/or the like. As will be pointed out below, the exact amount required will vary from subject to subject, depending on the species, age, and general condition of the subject, the severity of the condition or disease that is being treated, the particular composition used, its mode of administration, and the like. Thus, it is not possible to specify an exact "effective amount." However, an appropriate effective amount may be determined by one of ordinary skill in the art using only routine experimentation.

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The term "isolated" is intended to mean that a compound is separated from all or some of the components that accompany it in nature. "Isolated" also refers to the state of a compound separated from all or some of the components that accompany it during manufacture (e.g., chemical synthesis, recombinant expression, culture medium, and the like).

The term "antibody" (also used interchangeably with "immunoglobulin") encompasses polyclonal and monoclonal antibody preparations where the antibody may be of any class of interest (e.g., IgG, IgM, and subclasses thereof), as well as preparations including hybrid antibodies, altered antibodies, F(ab')$_2$ fragments, F(ab) molecules, Fv fragments, single chain fragment variable displayed on phage (scFv), single chain antibodies, single domain antibodies, diabodies, chimeric antibodies, humanized antibodies, and functional fragments thereof which exhibit immunological binding properties of the parent antibody molecule. In some embodiments, e.g., cancer therapy, antibodies that provide for complement-mediated killing and/or antibody-dependent cellular cytotoxicity (ADCC) are of interest. The antibodies described herein may be detectably labeled, e.g., with a radioisotope, an enzyme which generates a detectable product, a fluorescent protein, and the like. Detectable labels that find use in in vivo imaging are of interest. The antibodies may be further conjugated to other moieties, such as a cytotoxic molecule or other molecule (e.g., to provide for delivery of an anti-cancer drug to a cancer cell), members of specific binding pairs, e.g., biotin (member of biotin-avidin specific binding pair), and the like. The antibodies may also be bound to a support (e.g., a solid support), such as a polystyrene plate or bead, test strip, and the like.

Immunoglobulin polypeptides include the kappa and lambda light chains and the alpha, gamma (IgG$_1$, IgG$_2$, IgG$_3$, IgG$_4$), delta, epsilon and mu heavy chains or equivalents in other species. Full-length immunoglobulin "light chains" (usually of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

An immunoglobulin light or heavy chain variable region is composed of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, 1991, and Lefranc et al. IMGT, the international ImMunoGeneTics information System®. Nucl. Acids Res., 2005, 33, D593-D597)). A detailed discussion of the Kabat numbering system is provided on the World Wide Web at kabatdatabase.com/index.html. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The term "monoclonal antibody" refers to an antibody composition having a homogeneous antibody population. The term is not limited by the manner in which it is made. The term encompasses whole immunoglobulin molecules, as well as Fab molecules, F(ab')2 fragments, Fv fragments, single chain fragment variable displayed on phage (scFv), fusion proteins comprising an antigen-binding portion of an antibody and a non-antibody protein, and other molecules that exhibit immunological binding properties of the parent monoclonal antibody molecule. Methods of making and screening polyclonal and monoclonal antibodies are known in the art.

The term "specific binding of an antibody" or "antigen-specific antibody" in the context of a characteristic of an antibody refers to the ability of an antibody to preferentially bind to a particular antigen that is present in a homogeneous mixture of different antigens. In certain embodiments, a specific binding interaction will discriminate between desirable and undesirable antigens (or "target" and "non-target" antigens) in a sample, in some embodiments more than about 10 to 100-fold or more (e.g., more than about 1000- or 10,000-fold). In certain embodiments, the affinity between an antibody and antigen when they are specifically bound in an antibody-antigen complex is characterized by a $K_D$ (dissociation constant) of less than $10^{-6}$M, less than $10^{-7}$ M, less than $10^{-8}$ M, less than $10^{-9}$ M, less than $10^{-9}$ M, less than $10^{-11}$M, or less than about $10^{-12}$M or less.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Conservative amino acid substitutions in the context of an antibody disclosed herein are selected so as to preserve the interaction between the antibody and the protease of interest.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained.

The term "pharmaceutically acceptable carrier" as used herein refers to any suitable substance which provides a pharmaceutically acceptable vehicle for administration of a compound(s) of interest to a subject. "Pharmaceutically acceptable carrier" can encompass substances referred to as pharmaceutically acceptable diluents, pharmaceutically acceptable additives and pharmaceutically acceptable excipients.

The term "purified" is intended to mean a compound of interest has been separated from components that accompany it in nature and provided in an enriched form. "Purified" also refers to a compound of interest separated from components that can accompany it during manufacture (e.g., in chemical synthesis, recombinant expression, culture medium, and the like) and provided in an enriched form. Typically, a compound is substantially pure when it is at least 50% to 60%, by weight, free from organic molecules with which it is naturally associated or with which it is associated during manufacture. Generally, the preparation is at least 75%, more usually at least 90%, and generally at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, etc.

The term "subject" is intended to cover humans, mammals and other animals which contain uPA in any fashion. The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

In the context of cancer therapies and diagnostics described herein, "subject" or "patient" is used interchangeably herein to refer to a subject having, suspected of having, or at risk of developing a tumor. The cancer may be one associated with metastasis, where the metastatic cells or cells surrounding the same (e.g., stromal cells) secrete pro-uPA, which is then converted to uPA. Samples obtained from such subject are likewise suitable for use in the methods of the present disclosure.

As used herein, the terms "determining," "measuring," and "assessing," and "assaying" are used interchangeably and include both quantitative and qualitative determinations.

It is further noted that the claims may be drafted to exclude any optional or alternative element. As such, this statement is intended to serve as antecedent basis for use of such exclusive terminology as "solely", "only" and the like in connection with the recitation of claim elements, or the use of a "negative" limitation.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. To the extent a definition of a term set out in a document incorporated herein by reference conflicts with the definition of a term explicitly defined herein, the definition set out herein controls.

Anti-uPA antibodies are described first in greater detail, followed by descriptions of exemplary formulations and methods employing the same, as well as a discussion of representative applications in which the antibodies, formulations and methods of the present disclosure find use.

Anti-uPA ANTIBODIES

The present disclosure provides antibodies that specifically bind to urokinase-type plasminogen activator (uPA). The antibodies may be non-human antibodies (e.g., mouse antibodies, rabbit antibodies, or any non-human antibody), humanized antibodies, or fully human antibodies (e.g., a fully human recombinant antibody identified from a phage display library, or the like). Antibodies of the present disclosure bind to one or more epitopes of uPA. According to certain embodiments, the antibody binds to the heavy (B) chain of uPA and not the light (A) chain of uPA. Such an antibody may bind to the serine protease domain (SPD) of uPA. An antibody that binds to the SPD of uPA may bind to the active site of uPA, or may bind to a region outside of the active site. In certain aspects, the anti-uPA antibody does not bind to the autolysis loop of uPA. According to certain embodiments, the anti-uPA antibody does not bind to the activation domain of uPA. In certain aspects, the antibody specifically binds to urokinase-type plasminogen activator (uPA) and competes for binding to uPA with a uPA ligand. The uPA ligand may be a synthetic ligand of uPA (e.g., synthetic peptide ligand, a small molecule ligand, or the like) or a naturally occurring ligand such as plasminogen, fibronectin, PAI-1, uPAR, hepatocyte growth factor, or the like).

In certain aspects, the uPA ligand is a synthetic ligand, e.g., synthetic substrate or sybhetic inhibitor). A syntehtic ligand of uPA can be a small molecule, such as p-aminobenzamidine, or a synthetic peptide ligand (e.g., a synthetic peptide substrate or synthetic peptide inhibitor), such as synthetic peptide ligands having the amino acid sequence Glu-Gly-Arg, e.g., such as Glu-Gly-Arg-chloromethylketone (EGR-CMK), H-D-Glu-Gly-Arg-p-nitroanilide (S-2444) and the like. The uPA ligand may be plasminogen, fibronectin, PAI-1, uPAR, hepatocyte growth factor, or the like. In certain aspects, the antibody competes for binding to uPA with a uPA ligand, which uPA ligand binds to the active site of uPA without binding to an exosite of uPA (e.g., the ligand binds to the active site of uPA independent of any interactions with an exosite (e.g., a region outside of the active site) of uPA). Such exosite-independent uPA ligands may be a synthetic ligand for uPA. The antibodies provided by the present disclosure may include one or more (e.g., 1, 2, 3, 4, 5, or all 6) complementary determining regions (CDRs) set forth in Table 1, FIG. 11 and SEQ ID NOs:1-6, or conservative variants of one or more such CDRs.

According to certain embodiments, an anti-uPA antibody of the present disclosure binds to an epitope provided by the active site of uPA. In certain aspects, the antibody that binds to the active site of uPA interacts with one or more amino acids of uPA which are determinants for binding a tripeptide substrate to uPA. Such an amino acid(s) includes but is not limited to: an amino acid in the 51 pocket (e.g., Asp370, Ser371 and/or Gly399); an amino acid in the S2 pocket (e.g., His272); an amino acid in the S3 pocket (Leu270 and/or Ala271); an amino acids essential for catalysis (e.g., His224, Asp275 and/or Ser376); and any combination of such amino acids. Numbering of the amino acids is according to the uPA amino acid sequence shown in FIG. 12. Additional information regarding uPA amino acids involved in substrate binding is found, e.g., in Spraggon et al. (1995) *Structure* 3:681-691.

In certain aspects, provided is an antibody that competes for specific binding to uPA with plasminogen activator inhibitor type 1 (PAI-1), where binding of the antibody to uPA results in internalization of a complex that includes the antibody, uPA, and urokinase-type plasminogen activator receptor (uPAR). According to certain embodiments, this complex does not include PAI-1. In certain aspects, the antibody is antibody U33. The structural basis for recognition of uPA by PAI-1 has been elucidated via crystallographic analysis at 2.3-angstrom resolution (Lin et al. (2011) *J. Biol. Chem.* 286(9):7027-7032). The crystal structure reveals extensive interaction between the reactive center loop (RCL) of PAI-1 and catalytic sites within the active site of uPA. On the N-terminal side (P side) of the scissile bond, the P1 residue occupies the 51 specificity pocket of uPA, and further interacts with uPA through a well defined network of hydrogen bonds and Van der Waals interactions. The S2 pocket and S3 pocket of uPA are occupied by P2 and P3 of PAI-1, respectively. In sum, the interactions between PAI-1 and the uPA active site region account for approximately 64% of the total contact area.

Accordingly, in certain aspects, an anti-uPA antibody of the present disclosure may interact with and/or shield access to one or more catalytic sites within the active site of uPA. The anti-uPA antibody may interact with (e.g., occupy) one or more of the 51, S2, S3, and/or S4 pockets of uPA. According to one embodiment, a portion of the anti-uPA antibody occupies and/or shields access to the 51 pocket of uPA.

According to certain embodiments, provided is an antibody that specifically binds to uPA and competes for binding to uPA with a uPA ligand. In certain aspects, the uPA ligand is a synthetic ligand, e.g., a small molecule such as p-aminobenzamidine, or a synthetic peptide ligand, e.g., a synthetic peptide inhibitor such as Glu-Gly-Arg-chloromethylketone (EGR-CMK), a synthetic peptide substrate H-D-Glu-Gly-Arg-p-nitroanilide (S-2444) and the like, or any other synthetic substance capable of binding to and/or being cleaved by uPA. When the synthetic ligand is a synthetic peptide ligand, the ligand may include less than 20 amino acids, less than 15 amino acids, less than 10 amino acids, or less than 5 amino acids (e.g., 3 amino acids). In certain aspects, the synthetic peptide ligand is the uPA inhibitor Glu-Gly-Arg-chloromethylketone (EGR-CMK). In other aspects, the synthetic peptide ligand is H-D-Glu-Gly-Arg-p-nitroanilide (S-2444). In certain aspects, the antibody is the U33 Fab or an antibody having the binding characteristics of U33 Fab (e.g., an antibody having one or more (e.g., all) of the heavy and light chain CDRs of U33 Fab). The crystal structure of the catalytic domain of uPA complexed with EGR-CMK has been determined at 2.5-angstrom resolution (Spraggon et al. (1995) *Structure* 3:681-691). This structure reveals that EGR-CMK covalently binds to the active site of uPA to form a hemiketal structure. The C-terminal arginine of the inhibitor, EGR-CMK, is covalently linked via the carbonyl group to Ser195 and through its methyl group to His57. The arginine side chain of the inhibitor extends into the S1 pocket of uPA and makes a charge interaction with Asp189 at the base of the pocket. The glutamic acid of the inhibitor forms a salt bridge to Arg217 and can form a hydrogen bond to the nitrogen of Gly218. Accordingly, the antibody that specifically binds to uPA and competes with the uPA inhibitor Glu-Gly-Arg-chloromethylketone (EGR-CMK) for binding to uPA may interact with and/or shield access to one or more catalytic sites within the active site of uPA. For example, the anti-uPA antibody may interact with (e.g., occupy) one or more of the S1, S2, S3, and/or S4 pockets of uPA. According to one embodiment, the anti-uPA antibody occupies and/or shields access to the S1 pocket of uPA.

In certain aspects, the antibody competes for binding to uPA with a uPA ligand, which ligand binds to the active site of uPA without binding to an exosite of uPA (e.g., the ligand binds to the active site of uPA independent of any interactions with an exosite (e.g., a region outside of the active site of uPA).

According to certain embodiments, an anti-uPA antibody of the present disclosure may compete for specific binding to uPA with p-aminobenzamidine. For example, the antibody may be capable of discplacing p-aminobenzamidine from the S1 pocket of uPA. Such an antibody may interact with residues of the S1 pocket of uPA or one or more regions adjacent thereto, which residues interact with p-aminobenzamidine when p-aminobenzamidine is bound to uPA.

According to certain embodiments, an anti-uPA antibody of the present disclosure competes for binding to uPA with a uPA ligand (e.g., PAI-1 and/or a synthetic peptide ligand) and binds outside of the uPA active site. That is, an antibody of the present disclosure may specifically bind outside of the uPA active site (e.g., a non-active site portion of the serine protease domain), where the binding causes a conformational change in uPA that prevents binding of a uPA ligand to the active site of uPA. In some embodiments the uPA ligand is a synthetic uPA ligand. Such a conformational change may block entry of one or more portions of the uPA active site and prevent interactions between, e.g., PAI-1 and/or EGR-CMK with catalytic and/or non-catalytic residues within the uPA active site.

Any of the antibodies of the present disclosure described hereinabove or below may be specific for the active form of uPA (e.g, do not bind to the zymogen form of uPA). Any of the antibodies of the present disclosure described hereinabove or below may be specific for human uPA (e.g., do not bind to uPA from a non-human organism, such as murine uPA). Any of the antibodies of the present disclosure described hereinabove or below may be specific for the active form of human uPA.

In one embodiment, an anti-uPA antibody of the present disclosure comprises one or more CDRs of the amino acid sequence of the mature (i.e., missing signal sequence) heavy chain variable region (VH) of U33 set out in SEQ ID NO:7, or variants thereof. In some embodiments, the VH comprises the amino acid sequence from the beginning of the CDR1 to the end of the CDR3 of any one of the heavy chain of the foregoing antibodies.

In certain aspects, the anti-uPA antibody includes a heavy chain CDR1, CDR2 or CDR3 (HCDR1, HCDR2, HCDR3), each of which are independently selected from the CDR1 (SEQ ID NO:1), CDR2 (SEQ ID NO:2) and CDR3 (SEQ ID NO:3) regions of an antibody having a heavy chain variable region comprising the amino acid sequence of the VH region of U33 set out in SEQ ID NO:7, a nucleic acid encoding the VH region set out in SEQ ID NO:7, or encoded by a nucleic acid molecule encoding the VH region. It is further contemplated that an anti-uPA antibody of the present disclosure includes a heavy chain CDR1, CDR2 or CDR3, each of which are independently selected from the CDR1 (SEQ ID NO:1), CDR2 (SEQ ID NO:2) and CDR3 (SEQ ID NO:3) regions of an antibody having a heavy chain variable region comprising the amino acid sequence of the VH region set out in SEQ ID NO:7. In one embodiment, the anti-uPA antibody includes the CDR1 (SEQ ID NO:1), CDR2 (SEQ ID NO:2) and CDR3 (SEQ ID NO:3) regions of an antibody having a heavy chain variable region comprising the amino acid sequence of the VH region of U33 set out in SEQ ID NO:7.

According to certain embodiments, the amino acid sequence of the anti-uPA antibody includes one or more CDRs of the amino acid sequence of the mature (i.e., missing signal sequence) light chain variable region (VL) of U33 set out in SEQ ID NO:8, or variants thereof, including CDR grafted, modified, humanized, chimeric, or Human Engineered antibodies or any other variants described herein. In some embodiments, the VL comprises the amino acid sequence from the beginning of the CDR1 to the end of the CDR3 of the light chain of any one of the foregoing antibodies.

In certain aspects, the anti-uPA antibody includes a light chain CDR1, CDR2 or CDR3 (LCDR1, LCDR2, LCDR3), each of which are independently selected from the CDR1 (SEQ ID NO:4), CDR2 (SEQ ID NO:5) and CDR3 (SEQ ID NO:6) regions of an antibody having a light chain variable region comprising the amino acid sequence of the VL region of U33 set out in SEQ ID NO:8, a nucleic acid encoding the VL region set out in SEQ ID NO:8, or encoded by a nucleic acid molecule encoding the VL region. It is further contemplated that an anti-uPA antibody of the present disclosure includes a light chain CDR1, CDR2 or CDR3, each of which are independently selected from the CDR1 (SEQ ID NO:4), CDR2 (SEQ ID NO:5) and CDR3 (SEQ ID NO:6) regions of an antibody having a light chain variable region comprising the amino acid sequence of the VL region set out in SEQ ID NO:8. In one embodiment, the anti-uPA antibody includes the CDR1 (SEQ ID NO:4), CDR2 (SEQ ID NO:5) and CDR3 (SEQ ID NO:6) regions of an antibody having a light chain variable region comprising the amino acid sequence of the VL region of U33 set out in SEQ ID NO:8.

Antibodies of the present disclosure may have a heavy chain variable region polypeptide having a CDR1, CDR2, and CDR3 of the amino acid sequence of SEQ ID NO:7 as defined by Kabat et al. (supra). The present disclosure also encompasses antibodies having a heavy chain variable region polypeptide having a CDR1, CDR2, and CDR3 of the amino acid sequence of SEQ ID NO:7 numbered according to ImMunoGenTics (IMGT (supra)) numbering. Antibodies of the present disclosure may have a light chain variable region polypeptide having a CDR1, CDR2, and CDR3 of the amino acid sequence of SEQ ID NO:8 as defined by Kabat et al. (supra). Also encompassed are antibodies having a light chain variable region polypeptide having a CDR1, CDR2, and CDR3 of the amino acid sequence of SEQ ID NO:8 numbered according to ImMunoGenTics (IMGT; supra) numbering.

In another embodiment, the antibody comprises a mature heavy chain variable region as disclosed above, a mature light chain variable region as disclosed above, or a mature heavy chain variable region as disclosed above and a mature light chain variable region as disclosed above.

In certain aspects, an anti-uPA antibody of the present disclosure is a monoclonal antibody that retains any one, two, three, four, five, or six of HCDR1, HCDR2, HCDR3, LCDR1, LCDR2, or LCDR3 of U33, optionally including one or two mutations in any of such CDR(s), e.g., a conservative or non-conservative substitution, and optionally paired as set forth in Table 1.

TABLE 1

Complementarity determining regions of U33.

| Heavy Chain | U33 |
|---|---|
| HCDR1 | GFTFGDYAMS (SEQ ID NO: 1) |
| HCDR2 | FIRSKAYGGTTE (SEQ ID NO: 2) |
| HCDR3 | IRGANWN (SEQ ID NO: 3) |

| Light Chain | |
|---|---|
| LCDR1 | RSSQTLMNRNGNNFLD (SEQ ID NO: 4) |
| LCDR2 | LGSNRAP (SEQ ID NO: 5) |
| LCDR3 | MQRIEFPYT (SEQ ID NO: 6) |

Also provided is a monoclonal anti-uPA antibody that retains all of HCDR1 (SEQ ID NO:1), HCDR2 (SEQ ID NO:2) and HCDR3 (SEQ ID NO:3), or the heavy chain variable region of SEQ ID NO:7, optionally including one or two mutations in any of such CDR(s), optionally further comprising any suitable heavy chain constant region, e.g., IgG1, IgG2, IgG3, IgG4, IgM, IgA1, IgA2, or IgE, a human sequence thereof, or a hybrid thereof.

According to certain embodiments, an antibody of the present disclosure is a monoclonal antibody that retains all of LCDR1 (SEQ ID NO:4), LCDR2 (SEQ ID NO:5) and LCDR3 (SEQ ID NO:6), or the light chain variable region of SEQ ID NO:8, optionally including one or two mutations in any of such CDR(s), optionally further including any suitable light chain constant region, e.g., a kappa or lambda light chain constant region, a human sequence thereof, or a hybrid thereof.

In certain aspects, the anti-uPA antibody includes all three heavy chain CDRs of U33, all three light chain CDRs of U33, or all six CDRs of the heavy and light chains of U33, paired as set forth in Table 1. In certain embodiments, two heavy chain CDRs from the U33 may be combined with a third heavy chain CDR from a different antibody. Alternatively, a HCDR1 from the U33 Fab may be combined with a HCDR2 from a different antibody and a HCDR3 from yet another antibody, particularly where the CDRs are highly homologous. Similarly, two light chain CDRs from U33 may be combined with a third light chain CDR from a different antibody. Alternatively, an LCDR1 from the U33 Fab may be combined with a LCDR2 from a different antibody and a LCDR3 from yet another antibody, particularly where the CDRs are highly homologous.

According to certain embodiments, the anti-uPA antibody includes a polypeptide having an amino acid sequence at least about 90%, 91%, 92%, 93%, 94%, 95%, 96%, 97%, 98%, 99% or more identical to the heavy chain variable region set out in SEQ ID NO:7 and/or an amino acid sequence at least about 90%, 91%, 92%, 93%, 94%, 95%, 96%, 97%, 98%, 99% or more identical to the light chain variable region set out in SEQ ID NO:8. Such an antibody may further include at least one, two, three, four, five or all of HCDR1, HCDR2, HCDR3, LCDR1, LCDR2 or LCDR3. In some embodiments, the amino acid sequence with percentage identity to the heavy chain variable region may include one, two or three of the heavy chain CDRs. In other embodiments, the amino acid sequence with percentage identity to the light chain variable region may comprise one, two, or three of the light chain CDRs.

In certain aspects, an anti-uPA antibody is provided that includes a polypeptide having an amino acid sequence at least 90%, 91%, 92%, 93%, 94%, 95%, 96%, 97%, 98%, 99% or more identical to all three HCDRs of the heavy chain variable region set out in SEQ ID NO:7. Alternatively, or additionally, the anti-uPA antibody may include a polypeptide having an amino acid sequence at least 90%, 91%, 92%, 93%, 94%, 95%, 96%, 97%, 98%, 99% or more identical to all three LCDRs of the light chain variable region set out in SEQ ID NO:8. In a further embodiment, an antibody of the present disclosure may include a polypeptide having an amino acid sequence at least about 80%, 81%, 82%, 83%, 84%, 85%, 86%, 87%, 88%, 89%, 90%, 91%, 92%, 93%, 94%, 95%, 96%, 97%, 98%, 99% or more identical to all six CDRs in the heavy chain and light chain variable regions of U33 Fab as set out in SEQ ID NOs: 7 and 8, respectively.

Antibodies of the disclosure may include one, or two or more amino acid substitutions in the CDR regions of the antibody (e.g., non-conservative or conservative substitutions), e.g., as compared to U33.

According to one embodiment, the residues of the framework are altered. The heavy chain framework regions which may be altered lie within the regions surrounding the heavy chain CDR residues, and the residues of the light chain framework regions which may be altered lie within the regions surrounding the light chain CDR residues. An amino acid within the framework region may be replaced, for example, with any suitable amino acid identified in a human framework or human consensus framework.

In certain aspects, an anti-uPA antibody of the present disclosure binds to uPA (e.g., the active form of uPA, human uPA, or the active form of human uPA) with an affinity (Kd) of $10^{-6}$ M, $10^{-7}$ M, $10^{-8}$ M, $10^{-9}$ M, $10^{-10}$ M, $10^{-11}$ M, or $10^{-12}$ M or less (lower meaning higher binding affinity). According to certain embodiments, an anti-uPA antibody of the present disclosure binds to uPA (e.g., the active form of uPA, human uPA, or the active form of human uPA) with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% or more higher affinity (e.g., preferentially binds to uPA) compared to binding to any other protease, e.g., a protease selected from tPA, trypsin, chymotrypsin, elastase, hK2, PSA, KLK4, KLK7, hepsin, HGFA, MT-SP1, plasmin, thrombin, and combinations thereof.

An anti-uPA antibody of the present invention may bind to active human uPA with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% or more higher affinity (e.g., preferentially binds to active human uPA) compared to binding to inactive human uPA, or active or inactive uPA from a non-human organism.

In certain aspects, an anti-uPA antibody of the present disclosure specifically binds to the serine protease domain of uPA, and does not bind to the Kringle or EGF-like domains of the uPA chain A. For example, the anti-uPA antibody may occupy and/or bind to an epitope within or near the uPA active site of the serine protease domain of uPA (e.g., the S1 pocket of uPA), as described in more detail above.

Nucleic acids encoding any of the antibodies of the present invention are also provided. For example, the nuceic acid sequences encoding the U33 heavy and light chain variable polypeptides are provided in FIG. 11, panel B. the nucleic acids may be present in an expression vector for production of any antibody of the present disclosure in a cell.

Chimeric and Humanized Antibodies

Because chimeric or humanized antibodies are less immunogenic in humans than the parental non-human (e.g., mouse) monoclonal antibodies, they can be used for the treatment of humans with far less risk of anaphylaxis. Accordingly, in certain aspects, an anti-uPA antibody of the present disclosure is chimeric or humanized.

Chimeric monoclonal antibodies, in which the variable Ig domains of a non-human (e.g., mouse) monoclonal antibody are fused to human constant Ig domains, can be generated using standard procedures known in the art (See Morrison et al., Proc. Natl. Acad. Sci. USA 81, 6841-6855 (1984); and, Boulianne et al, Nature 312, 643-646, (1984)).

Humanized antibodies may be achieved by a variety of methods including, for example: (1) grafting the non-human complementarity determining regions (CDRs) onto a human framework and constant region (a process referred to in the art as humanizing through "CDR grafting"); (2) transplanting the entire non-human variable domains, but "cloaking" them with a human-like surface by replacement of surface residues (a process referred to in the art as "veneering"); or (3) substituting human amino acids at positions determined to be unlikely to adversely effect either antigen binding or protein folding, but likely to reduce immunogenicity in a human environment (e.g., HUMAN ENGINEERING™). In the present disclosure, humanized antibodies may include "humanized," "veneered," and/or "HUMAN ENGINEERED™" antibodies. These methods are disclosed in, e.g., Jones et al., Nature 321:522 525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31:169-217 (1994); Studnicka et al. U.S. Pat. No. 5,766,886; Studnicka et al., (Protein Engineering 7: 805-814, 1994; Co et al., J. Immunol. 152, 2968-2976 (1994); Riechmann, et al., Nature 332:323-27 (1988); and Kettleborough et al., Protein Eng. 4:773-783 (1991) each of which is incorporated herein by reference.

CDR grafting involves introducing one or more of the six CDRs from the mouse heavy and light chain variable Ig domains into the appropriate four framework regions of human variable Ig domains. This technique (Riechmann, et al., Nature 332:323-27 (1988)), utilizes the conserved framework regions (FR1-FR4) as a scaffold to support the CDR loops which are the primary contacts with antigen. A disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co et al., J. Immunol. 152, 2968-2976 (1994)).

Antibody Fragments

Any of the anti-uPA antibodies described elsewhere herein may be in the form of an antibody fragment. Antibody fragments comprise a portion of an intact full length antibody and can include an antigen binding or variable region of the intact antibody. Examples of antibody fragments include Fab; Fab'; F(ab')2; Fv fragments; diabodies; linear antibodies; single-chain antibody molecules (e.g., scFv); multispecific antibody fragments such as bispecfic, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; VHH containing antibodies; and other polypeptides formed from antibody fragments. See, e.g., Holliger & Hudson (Nat. Biotech. 23:1126-36 (2005)).

Papain digestion of antibodies produces two identical antigen-binding fragments, called "Fab" fragments, monovalent fragments consisting of the VL, VH, CL and CH domains each with a single antigen-binding site, and a residual "Fc" fragment, whose name reflects its ability to crystallize readily. Pepsin treatment yields a F(ab')2 fragment, a bivalent fragment comprising two Fab fragments linked by a disulfide bridge at the hinge region, that has two "Single-chain Fv" or "scFv" antibody fragments comprise the VH and VL domains of antibody, wherein these domains are present in a single polypeptide chain. The Fv polypeptide can further comprise a polypeptide linker between the VH and VL domains that enables the Fv to form the desired structure for antigen binding, resulting in a single-chain antibody (scFv), in which a VL and VH region are paired to form a monovalent molecule via a synthetic linker that enables them to be made as a single protein chain (Bird et al., Science 242:423-426, 1988, and Huston et al., Proc. Natl. Acad. Sci. USA 85:5879-5883, 1988). For a review of scFv see Pluckthun, in The Pharmacology of Monoclonal Antibodies, vol. 1 13, Rosenburg and Moore eds., Springer-Verlag, New York, pp. 269-315 (1994). An Fd fragment consists of the VH and CH1 domains.

Additional antibody fragments include a domain antibody (dAb) fragment (Ward et al., Nature 341:544-546, 1989) which consists of a VH domain. Diabodies are bivalent antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., Proc. Natl. Acad. Sci. USA 90:6444-6448, 1993, and Poljak et al., Structure 2:1121-1123, 1994). Diabodies can be bispecific or monospecific.

Antibody Conjugates

As described in more detail elsewhere herein, according to certain embodiments, the anti-uPA antibodies of the present disclosure result in internalization of a complex that includes the antibody, uPA, and urokinase-type plasminogen activator receptor (uPAR) (which complex may or may not include PAI-1). Antibodies having this feature find use in therapeutic and diagnostic (e.g., in vivo imaging, etc.) applications. For example, such an antibody may be conjugated to a payload, such as a therapeutic agent (e.g., a cytotoxic payload) or labeling agent (e.g., an in vivo imaging agent), where upon binding of the antibody to uPA and internalization of the resulting antibody/uPA/uPAR complex, the therapeutic or labeling agent is delivered specifically to the cytosol of target cells having surface-attached uPA/uPAR (e.g., metastatic or invasive cancer cells (e.g., castration-resistant prostate cancer cells), and/or stromal cells surrounding the same). The specific internalization of the therapeutic or labeling agent in cells having surface-attached uPA/uPAR reduces unwanted exposure of non-target cells to the therapeutic agent, and can reduce toxicity upon administration. Moreover, in imaging applications (e.g., in vivo imaging for diagnostic, prognostic, and/or any other purpose), specific internalization of a labeling agent into cells having surface-attached uPA/uPAR concentrates the labeling agent in such cells, thereby increasing the signal-to-noise ratio and diagnostic/prognostic value of the resulting images. Moreover, the internalization feature of anti-uPA antibody conjugates of the present disclosure permits their administration at lower amounts/concentrations than a conjugate that includes an anti-uPA antibody that does not result in such internalization, due to the therapeutic or labeling agent being "concentrated" in the target cells of interest (e.g., metastatic or invasive cancer cells, and/or stromal cells surrounding the same).

Accordingly, any anti-uPA antibody described herein may be in unconjugated form, or may be conjugated directly to an agent, such as a therapeutic and/or labeling (e.g., diagnostic) agent, or may be conjugated indirectly to carrier polymers comprising such other therapeutic or labeling agents. In some embodiments, the antibody is conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Suitable chemotherapeutic agents include: daunomycin, doxorubicin, methotrexate, and vindesine (Rowland et al., (1986) supra). Suitable toxins include: bacterial toxins such as diphtheria toxin; plant toxins such as ricin; small molecule toxins such as geldanamycin (Mandler et al J. Natl. Cancer Inst. 92(19):1573-81 (2000); Mandler et al., Bioorg. Med. Chem. Letters 10:1025-1028 (2000); Mandler et al., Bioconjugate Chem. 13.786-91 (2002)), maytansinoids (EP 1391213; Liu et al., Proc. Natl. Acad. Sci. USA 93:8618-23 (1996)), auristatins (Doronina et al., Nat. Biotech. 21: 778-84 (2003) and calicheamicin (Lode et al., Cancer Res. 58:2928 (1998); Hinman et al., Cancer Res. 53:3336-3342 (1993)).

Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are known; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

In certain aspects, the labeling agent of an anti-uPA antibody conjugate of the present disclosure is a labeling agent that finds use in in vivo imaging, such as near-infrared (NIR) optical imaging, single-photon emission computed tomography (SPECT)/CT imaging, or the like. Labeling agents that find use in such applications include, but are not limited to, fluorescent labels and radioisotopes, or the like. In certain aspects, the labeling agent is a multi-modal in vivo imaging agent that permits in vivo imaging using two or more imaging approaches (e.g., see Thorp-Greenwood and Coogan (2011) *Dalton Trans.* 40:6129-6143).

Conjugation of antibody moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, and can be about 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate. Examples of agents to which the antibody can be conjugated include any of the cytotoxic, chemotherapeutic agents described herein.

Conjugated antibodies can be prepared by directly conjugating an antibody component with a therapeutic agent or labeling agent. The general procedure is analogous to the indirect method of conjugation except that a therapeutic or labeling agent is directly attached to an oxidized antibody component. For example, a carbohydrate moiety of an antibody can be attached to polyethyleneglycol to extend half-life.

A therapeutic or labeling agent can be attached at the hinge region of a reduced antibody component via disulfide bond formation, or using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Pharmaceutical Compositions

Also provided by the present disclosure are pharmaceutical compositions that include any of the anti-uPA antibodies described herein, or any of the conjugates described herein, and a pharmaceutically acceptable carrier.

Pharmaceutical compositions of the present disclosure containing an anti-uPA antibody or conjugate of the present disclosure as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present disclosure.

Formulation of the pharmaceutical compositions of the present disclosure will vary according to the route of administration selected (e.g., solution, emulsion). An appropriate composition comprising the antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the anti-uPA antibodies of the present disclosure are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibody or conjugate may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulation herein may also contain more than one active compound (e.g., a second active agent in addition to the anti-uPA antibody or conjugate thereof) as necessary for the particular indication being treated (e.g., cancer), and which may be selected to complementary activities that do not adversely affect each other. Such molecules are suitably present in combination in amounts that are effective for the purpose intended.

The anti-uPA antibodies of the present disclosure may be lyophilized for storage and reconstituted in a suitable carrier prior to use. This technique has been shown to be effective with conventional immunoglobulins. Any suitable lyophilization and reconstitution techniques can be employed. Lyophilization and reconstitution can lead to varying degrees of antibody activity loss and that use levels may have to be adjusted to compensate.

Methods of Production

As discussed above, the present disclosure provides antibodies that specifically bind to uPA. Such antibodies are highly specific for binding to uPA. Example methods of making an anti-uPA antibody are presented below.

Antibodies can be prepared using a wide variety of techniques known in the art including the use of hybridoma, recombinant, and phage display technologies, or a combination thereof. For example, antibody may be made and isolated using methods of phage display. The antibody may also be isolated from sera of an animal host immunized with an immunogenic composition comprising uPA, which encompasses whole proteins and fragments thereof. Exemplary antibodies include an isolated antibody capable of specifically binding to uPA (e.g., the active form of human uPA, where the antibody competes for specific binding to uPA with PAI-1 or EGR-CMK, and/or results in internalization of a uPA/uPAR complex, which complex may not include PAI-1).

The antigen that coats the wells for phage display panning or the immunogenic composition used to elicit the antibody of the present disclosure may comprise an aggregate of one or more antigens. The method may involve exposing antigens to an aggregating condition so as to form an aggregate. Thus the methods of production described above may further include a step of forming an aggregate of the isolated antigens. Examples of the aggregating conditions include heating, addition of an excipient that facilitates aggregation, and the like.

Antigens used to coat the wells for phage panning or to elicit antibodies of the present disclosure may be conjugated to another molecule. For example, the antigen can be conjugated to a second molecule such as a peptide, polypeptide, lipid, carbohydrate and the like that aids in solubility, storage or other handling properties, cell permeability, half-life, controls release and/or distribution such as by targeting a particular cell (e.g., neurons, leucocytes etc.) or cellular location (e.g., lysosome, endosome, mitochondria etc.), tissue or other bodily location (e.g., blood, neural tissue, particular organs etc.).

A particular embodiment of an antigen conjugated to a second molecule is where the second molecule is an immunomodulator. "Immunomodulator" is a molecule that directly or indirectly modifies an immune response. A specific class of immunomodulators includes those that stimulate or aid in the stimulation of an immunological response. Examples include antigens and antigen carriers such as a toxin or derivative thereof, including tetanus toxoid.

Phage Display

Phage display is used for the high-throughput screening of protein interactions. Phages may be utilized to display antigen-binding domains expressed from a repertoire or combinatorial antibody library (e.g., human or murine). Phage expressing an antigen binding domain that binds the protease of interest can be selected or identified with the protease of interest, e.g., using labeled uPA or uPA bound or captured to a solid surface or bead. Phage used in these methods are typically filamentous phage including fd and M13 binding domains expressed from phage with Fab, Fv (individual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 2000, 21:371; Nagy et al. *Nat. Med.* 2002, 8:801; Huie et al., *Proc. Natl. Acad. Sci. USA* 2001, 98:2682; Lui et al., *J. Mol. Biol.* 2002, 315:1063, each of which is incorporated herein by reference. Several publications (e.g., Marks et al., *Bio/Technology* 1992, 10:779-783) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes et al., *Nat. Biotechnol.* 2000, 18:1287; Wilson et al., *Proc. Natl. Acad. Sci. USA* 2001, 98:3750; or Irving et al., *J. Immunol. Methods* 2001, 248:31). Cell surface libraries may be screened for antibodies (Boder et al., *Proc. Natl. Acad. Sci. USA* 2000, 97:10701; Daugherty et al., *J. Immunol. Methods* 2000, 243:211). Such procedures provide alternatives to traditional hybridoma techniques for the isolation and subsequent cloning of monoclonal antibodies. See the Examples section below.

In phage display methods, functional antibody domains are displayed on the surface of phage particles which carry the polynucleotide sequences encoding them. For example, DNA sequences encoding heavy chain variable (VH) and light chain variable (VL) regions are amplified or otherwise isolated from animal cDNA libraries (e.g., human or murine cDNA libraries of lymphoid tissues) or synthetic cDNA libraries. The DNA encoding the VH and VL regions may be joined together by an scFv linker by PCR and cloned into a phagemid vector (e.g., p CANTAB 6 or pComb 3 HSS). The vector is electroporated in *E. coli* and the *E. coli* is infected with helper phage. The VH or VL regions are usually recombinantly fused to either the phage gene III or gene VIII. Phage expressing an antigen binding domain that binds to an antigen of interest (e.g., the serine protease domain of uPA) can be selected or identified with antigen, e.g., using labeled antigen or antigen bound or captured to a solid surface or bead.

Additional examples of phage display methods that may be used to make the antibodies include those disclosed in PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the references listed above, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al., *BioTechniques* 1992, 12:864-869; and Sawai et al., *AJRI* 1995, 34:26-34; and Better et al., *Science* 1988, 240:1041-1043 (said references incorporated by reference in their entireties).

Immunization and Antibody Production

The method of eliciting antibodies in a host animal involves administering an effective amount of uPA or a fragment thereof as antigens described above to the host animal (i.e., a suitable mammal such as a mouse, rabbit or guinea pig, or a suitable avian, such as a chicken) to elicit production of an antibody that specifically binds to uPA. Methods of immunizing animal, including the adjuvants used, booster schedules, sites of injection, suitable animals, etc. are well understood in the art, e.g., Harlow et al. (*Antibodies: A Laboratory Manual*, First Edition (1988) Cold spring Harbor, N.Y.), and administration of living cells to animals has been described for several mammals and birds, e.g., McKenzie et al (*Oncogene* 4:543-8, 1989), Scuderi et al (*Med. Oncol. Tumor Pharmacother* 2:233-42, 1985), Roth et al (Surgery 96:264-72, 1984) and Drebin et al (*Nature* 312:545-8, 1984). Next, a population of antibody producing cells is generated. In one embodiment, the population of cells is produced using hybridoma methods that well known to one of skill in the art (see, e.g., Harlow *Antibodies: A Laboratory Manual*, First Edition (1988) Cold Spring Harbor, N.Y.). Cells are fused to immortalized cells, such as myeloma cells or transformed cells, which are capable of replicating indefinitely in cell culture, thereby producing an immortal, immunoglobulin-secreting cell line. The immortal cell line utilized can be selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT). In alterative embodiments, populations of cells expressing monoclonal antibodies may be made using phage display methods.

Anti-uPA antibodies, including antigen binding fragments of anti-upA antibodies, may also be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library can be constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Phage Panning and Screening

Once the population of antibody-producing cells or phages is produced, the antibodies are screened using one or a combination of a variety of assays. In general, these assays are functional assays, and may be grouped as follows: assays that detect an antibody's binding affinity or specificity, and assays that detect the ability of an antibody to initialize or inhibit a process.

For example, the antigen is coupled to beads or wells or other solid support and incubated with phage displaying the antibody of interest. After washings, bound phage is then recovered by inoculation of log phase E. coli cells. The cells are grown and expanded with helper phage. Steps are repeated for the amplification of tightly bound phages. The phage-infected E. coli colonies after several round of enrichment are harvested and Fab antibodies are purified from the periplasmic fractions. The purified antibodies are then analyzed in accordance with methods known in the art. Certain exemplary examples are detailed below.

The population of antibody isolated from phage-infected cells or hybridomas is further analyzed and/or screened for binding to a single antigen (i.e., antigens that are not mixed with other antigens of the plurality of antigens) of the plurality of antigens in vitro or in situ (e.g. on cells). Immunospecific binding may be carried out according to methods routine and known in the art. The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. See, e.g., Ausubel et al, eds, 1994, Current Protocols in Molecular Biology, Vol. 1, John Wiley & Sons, Inc., New York, which is incorporated by reference herein in its entirety.

Antibodies of the present disclosure may also be screened in vivo. The method involves administering an anti-uPA antibody to an animal model for a disease or condition and determining the effect of the antibody on the disease or condition of the model animal. In vivo assays of the invention include controls, where suitable controls include a sample in the absence of the antibody. Generally, a plurality of assay mixtures is run in parallel with different antibody concentrations to obtain a differential response to the various concentrations. Typically, one of these concentrations serves as a negative control, i.e., at zero concentration or below the level of detection.

A monoclonal antibody of interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a monoclonal antibody of interest will cause a subject animal to be more similar to an equivalent animal that is not suffering from the disease or condition. Antibodies that have therapeutic value that have been identified using the methods and compositions of the invention are termed "therapeutic" antibodies.

Selected monoclonal antibodies of interest can be expanded in vitro, using routine tissue culture methods, or in vivo, using mammalian subjects. For example, pristane-primed mice can be inoculated with log phase hybridoma cells in PBS for ascites production. Ascites fluid can be stored at −70° C. prior to further purification.

Methods of Screening

A screening method provided by the present disclosure may involve the use of a phage library to screen for an antibody that specifically binds to uPA, and optionally having any of the additional features described herein (competes for uPA binding with PIA-1 and/or ERG-CMK, and/or results in internalization of a uPA/uPAR complex, which complex may not include PAI-1). The binding agent may be selected for its potent inhibition of uPA and/or its specific binding affinity. The method may be executed according to the phage display method described above.

Briefly, uPA or a fragment thereof may be immobilized on an ELISA plate or on beads through a covalent or non-covalent interaction, such as hydrophobic adsorption, biotin-avidin interaction, and $Ni^{2+}$-6xHis interaction. The phage library is then incubated with the immobilized antigen/protease, washed, and recovered. During panning and selection, the bound phage is recovered and amplified in E. coli. Multiple successive selection rounds ensure a selection of a phage displaying a polypeptide that acts as an antibody specific for uPA. The stringency of the washes increases over a number of rounds (e.g. three). Many techniques well known in the art may be employed to increase the specificity of the recovered phage. Examples include increased wash times, increased detergent concentrations, increased salt concentrations, and inclusion of known macromolecular inhibitors (e.g., small peptidic substrates, BPTI, Ecotin, and/or previously identified antibody inhibitors). Identification of inhibitory antibodies may include ELISAs and inhibition assays. Details on the assays to be performed in the method for selecting and isolating an anti-uPA antibody are discussed above.

Also contemplated by the present disclosure is a library of nucleic acid constructs encoding the candidate anti-uPA antibodies described herein. The library encodes a plurality of candidate anti-uPA antibodies that may have one or more polypeptide regions in common (e.g. a heavy chain CDR3) and at least one other polypeptide region that varies among the population.

Diagnostics Methods

The present disclosure provides a method of detecting uPA in vivo, or in a biological sample in situ or isolated from a subject. The methods are useful to both diagnostic and prognostic pruposes. The methods generally involve contacting a sample comprising a cell with an anti-uPA antibody; and detecting binding of the antibody to a cell in the sample. The cell can be in vivo (e.g., a tumor or stromal cell in a human subject), in vitro (where the cell is in a biological sample obtained from a subject suspected for having cancer cells), a subject undergoing treatment, and/or a subject being tested for susceptibility to treatment.

The anti-uPA antibodies or conjugates thereof can be used to detect uPA in a biological sample of a subject having or suspected of having cancerous cells. Such diagnostics can be useful to identify patients amenable to the therapies disclosed herein, and/or to monitor tumor/metastatic progression, response to therapy, and/or the like.

Suitable immunodiagnostic techniques include, but are not necessarily limited to, both in vitro and in vivo (imaging) methods. The phrase "in vivo imaging" as used herein refers to methods of detecting the presence of uPA (e.g. detectably labeled U33) in a whole, live mammal. Optically detectable proteins such as fluorescent antibodies, radioisotope-conjugated antibodies, luciferase-conjugated antibodies, and the like may be detected by in vivo imaging. Methods for using luciferases for real-time imaging of luciferase expression in live animals can be readily adapted for use in the methods disclosed herein (e.g., Greer L F et al., *Luminescence* 2002, 17: 43-74). In vivo imaging of fluorescent proteins in live animals is described in, e.g., Hoffman, *Cell Death and Differentiation* 2002, 9:786-789. See Example 13 for details. In vivo imaging may be used to provide 2-D as well as 3-D images of a mammal. Radiolabeled antibodies, for example, may be administered to a subject and the subject imaged with a gamma camera. Charge-coupled device cameras, CMOS, or 3D tomographers may used to carry out in vivo imaging. For example, Burdette J E *Journal of Mol. Endocrin.*, 40: 253-261, 2008, reviews utilizing computed tomography, magnetic resonance imaging, ultrasonography, positron emission tomography, single-photon emission computed tomography (SPECT), etc., for in vivo imaging. SPECT can also be used with an integrated x-ray CAT (CT) scanner (SPECT/CT) in the methods. In certain aspects, the diagnostic methods utilize near-infrared (NIR) imaging. The information from many in vivo imaging methods as those described above can provide 3D distribution of the antibodies in the subject. See the Examples section below for more details.

Where the methods are in vitro, the biological sample can be any sample in which uPA may be present, including but not limited to, blood samples (including whole blood, serum, etc.), tissues, whole cells (e.g., intact cells), and tissue or cell extracts. For example, the assay can involve detection of a protease on cells in a histological tissue sample. For example, the tissue sample may be fixed (e.g., by formalin treatment) and may be provided embedded in a support (e.g., in paraffin) or frozen unfixed tissue.

Assays can take a wide variety of forms, such as competition, direct reaction, or sandwich type assays. Exemplary assays include Western blots; agglutination tests; enzyme-labeled and mediated immunoassays, such as enzyme-linked immunosorbent assays (ELISAs); biotin/avidin type assays; radioimmunoassays; immunoelectrophoresis; immunoprecipitation, and the like. The reactions generally include detctable labels such as fluorescent, chemiluminescent, radioactive, enzymatic labels or dye molecules, or other methods for detecting the formation of a complex between antigen in the sample and the antibody or antibodies reacted therewith.

The assays can involve separation of unbound antibody in a liquid phase from a solid phase support to which antigen-antibody complexes are bound. Solid supports which can be used include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Where a solid support is used, the solid support is usually first reacted with a solid phase component (e.g., an anti-uPA antibody) under suitable binding conditions such that the component is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies to a support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antibodies, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After reacting the solid support with the solid phase component, any non-immobilized solid-phase components are removed from the support by washing, and the support-bound component is then contacted with a biological sample suspected of containing a serin protease under suitable binding conditions. After washing to remove any non-bound ligand, a secondary binder moiety is added under suitable binding conditions, wherein the secondary binder is capable of associating selectively with the bound ligand. The presence or absence of the secondary binder can then be detected using techniques well known in the art.

An ELISA method can be used, where the wells of a microtiter plate are coated with a an anti-uPA antibody of the present disclosure. A biological sample containing or suspected of containing a protease (e.g., a tumor cell expressing uPA), is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound uPA from a biological sample can be readily detected using a secondary binder comprising an antibody directed against the antibody ligands. For example, a number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and uPA form complexes under precipitating conditions. For example, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing uPA to provide for formation of particle-antibody-uPA complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

The test sample used in the diagnostics assays can be any sample in which uPA may be present, including but not limited to, blood samples (including whole blood, serum, etc.), tissues, whole cells (e.g., intact cells), and tissue or cell extracts containing cells (e.g., tissue, isolated cells, etc.), a cell lysate (i.e., a sample containing non-intact cells), where each type of sample can contain elements of both types (e.g., a sample of cells can contain cell lysates, and vice versa). In some embodiments, particularly as in embodiments involving detection of cancer cells, it may be desirable to conduct the assay using a sample from the subject to be diagnosed that contains intact, living cells. uPA detection can then be assessed on an extracellular surface of the cells, and can further be assessed during cell division.

Diagnostic assays can also be conducted in situ. For example, anti-uPA antibodies can be detectably labeled, administered to a subject suspected of having a cancer characterized by uPA activity, and bound detectably labeled antibody detected using imaging methods available in the art.

The diagnostic assays described herein can be used to determine whether a subject has a cancer that is more or less amenable to therapy using antibody-based therapy, as well as monitor the progress of treatment in a subject. It also may be used to assess the course of other combination therapies (e.g., anti-uPA antibody therapy) as described in (U.S. Ser. No. 11/645,255 and PCT Application No. US2006/048850; incorporated herein by reference). Thus, the diagnostic assays can inform selection of therapy and treatment regimen by a clinician.

The protease of interest can be detected by detection of specific binding of an antibody, e.g., a monoclonal antibody (mAb) that has the antigen-binding specificity of U33. In this embodiment, uPA may be present on the cell surface at any stage of the cell cycle, including during cell division. In some instances, cancers that present the antigen during cell division may present a lower or no detectable level of the antigen when the cell is quiescent (i.e., not undergoing cell division). The antigen can also be detected in a permeabilized test cell. For example, a test cancer cell that exhibits a pattern of staining with a U33 Fab (or an antibody having the antigen binding specificity of U33) that is distinct from a pattern of antibody staining in a normal cell is identified as a cancerous cell that exhibits a U33-reactive antigen. Such cancers are thus amenable to therapy with an antibody that specifically binds the U33-reactive antigen (e.g., the mAb U33).

The above-described assay reagents, including the antibodies generated by immunization with uPA according to the methods described previously, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Methods of Treating uPA-Related Disorder

The present disclosure provides methods of treating a disorder (e.g., cancer) related to the activity of uPA. The methods generally involve administering to a subject in need thereof a therapeutically effective amount of any anti-uPA antibody or conjugate described herein, alone (e.g., in monotherapy) or in combination (e.g., in combination therapy) with one or more additional therapeutic agents. In certain aspects, the methods include treating a uPA-related disorder (e.g., cancer) by administering to a patient in need thereof a therapeutically effective amount of an anti-uPA antibody (e.g., an antibody of the present disclosure having any of the competitive binding and/or internalization features described herein) that specifically binds to the active form of human uPA, and that reduces or inhibits growth and/or invasiveness of cells having surface-attached uPA.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition (e.g., cancer) being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells, or so as to protect against disease caused by bacterial infection, which protection can include elimination of detectable bacterial cells; and/or (iii) relief, that is, causing the regression of clinical symptoms.

A variety of hosts are treatable according to the methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Prodrugs of the antibody composition of the present disclosure are also contemplated in the methods described herein. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

Antibody and conjugate compositions/formulations described herein may be administered to a subject (e.g. a human patient) to, for example, reduce the viability and/or invasiveness of cancerous cells, e.g., to reduce tumor size or metastasis, reduce tumor load, and/or improve the clinical outcome in patients. In certain aspects, antibody compositions can be used to disrupt the cell cycle of the cancer cell, and facilitate entry of the cell into apoptosis, e.g., by inducing cancerous cells to enter the pre-G0 cell cycle phase. The methods relating to cancer contemplated herein include, for example, use of antibody therapy alone or in combination with anti-cancer vaccine or therapy, as well as use of antibodies generated using uPA antigens in anti-cancer vaccines (e.g., by passive immunization) or therapies. The methods are useful in the context of treating or preventing a wide variety of cancers. uPA-related cancers that may be treated using the treatment methods of the present disclosure include, but are not limited to, prostate cancer (e.g., castration-resistant prostate cancer), breast cancer, gastric cancer, colorectal cancer, esophageal cancer, renal cancer, endometrial cancer, ovarian cancer, any other uPA-related cancer, and/or combinations thereof.

In certain embodiments, the antibody compositions may be advantageously used in an anti-cancer therapy, particularly where the cancerous cells present an active uPA on an extracellularly accessible cell surface. One example is a cancer that presents a U33-reactive antigen. Cancers that present a U33-reactive antigen can be identified by methods known in the art. Exemplary methods of detection and diagnosis are described elsewhere herein.

Cancers particularly amenable to antibody therapy can be identified by examining markers of cellular proliferation (e.g., Ki-67 antigen) and/or invasiveness, e.g., by examining the presence/accessibility of active uPA bound by U33 or by other anti-uPA antibodies provided by the present disclosure (e.g., as in an in vitro assay).

For example, the presence of an active uPA in normal human tissue appears to be transient and low abundance. It is prevalent primarily in abnormal cells, such as metastasing cancer cells of epithelial origin. Since expression of high levels of active uPA exists predominantly in cancer cells, treatment with antibody compositions can be used to detect the presence and localize cancer growth, induce cytotoxicity, and block tumor growth. In addition, antibody compositions can be used therapeutically to effect/prevent adhesion and invasion of cancer cells in other tissues.

Dosage

In the methods of the present disclosure, an effective amount of anti-uPA antibody (or conjugate including the same) is administered to a subject in need thereof. For example, in some embodiments, the anti-uPA antibody or conjugate inhibits growth, metastasis and/or invasiveness of a cancer cell(s) in a host when the anti-uPA antibody or conjugate is administered in an effective amount. The amount administered varies depending upon the goal of the administration, the health and physical condition of the individual to be treated, age, the taxonomic group of individual to be treated (e.g., human, non-human primate, primate, etc.), the degree of resolution desired, the formulation of the anti-uPA antibody or conjugate, the treating clinician's assessment of the medical situation, and other relevant factors. It is expected that the amount will fall in a relatively broad range that can be determined through routine trials. For example, the amount of the anti-uPA antibody or conjugate employed to inhibit cancer cell growth, metastasis and/or invasiveness is not more than about the amount that could otherwise be irreversibly toxic to the subject (i.e., maximum tolerated dose). In other cases the amount is around or even well below the toxic threshold, but still in an immunoeffective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the antibody or conjugate, and thus based on the disposition of the composition within the subject. This includes consideration of the route of administration as well as dosage amount, which can be adjusted for, e.g., parenteral (applied by routes other than the digestive tract for systemic or local effects) applications. For instance, administration of a the anti-uPA antibody or conjugate is typically via injection and often intravenous, intramuscular, intratumoral, or a combination thereof.

The anti-uPA antibody or conjugate may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g, by infusion) can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. The anti-uPA antibody or conjugate can also be administered as part of a combination therapy, in which at least one of an immunotherapy, a cancer chemotherapy or a radiation therapy is administered to the subject.

Disposition of the antibody or conjugate and its corresponding biological activity within a subject is typically gauged against the fraction of antibody present at a target of interest. For example, an antibody once administered can accumulate with a glycoconjugate or other biological target that concentrates the material in cancer cells and cancerous tissue. Thus dosing regimens in which the antibody is administered so as to accumulate in a target of interest over time can be part of a strategy to allow for lower individual doses. This can also mean that, for example, the dose of antibody that are cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the IC50 of a given antibody for inhibiting or binding uPA. By "IC50" is intended the concentration of a drug required for 50% inhibition in vitro. Alternatively, the effective amount can be gauged from the EC50 of a given antibody concentration. By "EC50" is intended the plasma concentration required for obtaining 50% of a maximum effect in vivo.

In general, with respect to the anti-uPA antibody or conjugate of the present disclosure, an effective amount is usually not more than 200× the calculated IC50. Typically, the amount of an antibody or conjugate that is administered is less than about 200×, less than about 150×, less then about 100× and many embodiments less than about 75×, less than about 60×, 50×, 45×, 40×, 35×, 30×, 25×, 20×, 15×, 10× and even less than about 8× or 2× than the calculated IC50. In one embodiment, the effective amount is about 1× to 50× of the calculated IC50, and sometimes about 2× to 40×, about 3× to 30× or about 4× to 20× of the calculated IC50. In other embodiments, the effective amount is the same as the calculated IC50, and in certain embodiments the effective amount is an amount that is more than the calculated IC50.

An effecteve amount may not be more than 100× the calculated EC50. For instance, the amount of antibody or conjugate that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated EC50. In one embodiment, the effective amount is about 1× to 30× of the calculated EC50, and sometimes about 1× to 20×, or about 1× to 10× of the calculated EC50. In other embodiments, the effective amount is the same as the calculated EC50, and in certain embodiments the effective amount is an amount that is more than the calculated EC50.

Effective amounts can readily be determined empirically from assays, from safety and escalation and dose range trials, individual clinician-patient relationships, as well as in vitro and in vivo assays such as those described herein and illustrated in the Examples section, below.

The IC50 may be calculated by inhibiting antibody binding in vitro. This aspect can be carried out by assessing the ability of the antibody of interest to inhibit U33 Fab binding to uPA. In general, the procedure is carried out by standard ELISA in which the plates are coated with uPA, e.g., at a suitable concentration, and then processed and employed to determine inhibition of antibody binding and the IC50. These antibodies and others suitable for various aspects of this purpose can be employed.

Routes of Administration

In practicing the methods, routes of administration (path by which the anti-uPA antibody or conjugate is brought into a subject) may vary, where representative routes of administration for the anti-uPA antibody or conjugate are described in greater detail below. The anti-uPA antibody or conjugate alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

Kits & Systems

Also provided are kits and systems that find use in practicing the methods, as described above. For example, kits and systems may include one or more of the compositions described herein, such as an anti-uPA antibody (e.g. U33), a nucleic acid encoding the same (especially a nucleic acid encoding a CDR of a heavy and/or light chain of U33), or a recombinant cell containing the same. Other optional components of the kit include: buffers, etc., for administering the anti-uPA antibody, and/or for performing a diagnostic assay. The recombinant nucleic acids of the kit may also have restrictions sites, multiple cloning sites, primer sites, etc to facilitate their ligation to constant regions of non-U33 encoding nucleic acids. The various components of the kit may be present in separate containers or certain compatible components may be pre-combined into a single container, as desired.

The kits and systems for practicing the methods may include one or more pharmaceutical formulations that include the antibody compositions described herein. As such, the kits may include a single pharmaceutical composition present as one or more unit dosages. In yet other embodiments, the kits may include two or more separate pharmaceutical compositions.

In addition to the above components, the kits may further include instructions for practicing the methods. These instructions may be present in the kits in a variety of forms, one or more of which may be present in or on the kit. One form in which these instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

A kit may be provided for use in treating a host suffering from, e.g., a cellular proliferative disease. This kit includes a pharmaceutical composition comprising antibody specific for uPA (e.g., the active form of human uPA), and instructions for the effective use of the pharmaceutical composition in a method of treating a host suffering from a cancerous condition by inhibiting the growth of a cancer cell in a subject. Such instructions may include not only the appropriate handling properties, dosing regiment and method of administration, and the like, but can further include instructions to optionally screen the subject for an active uPA associated with the disease. This aspect can assist the practitioner of the kit in gauging the potential responsiveness of the subject to treatment with an antibody of the present disclosure, including timing and duration of treatment relative to the type and growth stage of the cancer. Thus in another embodiment, the kit may further include an antibody (e.g., U33) or other reagent for detecting an active uPA on an extracellularly accessible surface of a cancer cell. In another embodiment, the kit includes antibody that comprises a conjugate with a detectable label, such as a label suitable for in vivo imaging, e.g., a fluorophore, radionuclide, and/or the like.

The term "system" as employed herein refers to a collection of antibodies described herein and one or more second therapeutic agents, present in single or disparate compositions that are brought together for the purpose of practicing the methods. For example, separately obtained antibody specific to uPA and chemotherapy dosage forms brought together and coadministered to a subject are a system according to the present disclosure.

The following examples further illustrate the present invention and should not be construed as in any way limiting its scope.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Identification of uPA in Prostate Cancer

Quantitative PCR (qPCR) was performed to determine plasminogen activation system (PAS) expression in prostate cancer cell lines and to correlate expression with androgen receptor (AR) status and cell line aggressiveness (FIG. 1, panel A). PAS expression was observed in the AR negative, aggressive metastatic cell lines PC3 and DU145. No expression was observed in AR positive prostate cancer cells lines, normal prostate epithelial cells (PrEC), or in the bladder cancer cell line TSU. mRNA expression for uPAR and uPA were highest in PC3, while DU145 expressed significantly higher PAI-1. PC3 and DU145 cells were cultured in 5% $O_2$ to mimic the $O_2$ deprived environment of prostate cancers and the levels of the PAS were analyzed (FIG. 1, panel B) (Stewart et al. (2010) *BJU Int* 105, 8-13). After 72 hrs, hypoxia had induced a two-fold expression increase of the PAS members in PC3. DU145 was less affected by hypoxia with only uPAR expression significantly increased. Under normal oxygenation conditions, PC3 expressed more uPA mRNA than DU145, and this result was corroborated at the protein level by IHC using a commercially available antibody (sc-14019) that recognized total uPA (zymogen uPA, active uPA and PAI-1 bound uPA) (FIG. 1, panel C). Staining in the PC3 xenograft section with sc-14019 was greater than the DU145 xenograft section for total uPA. Total uPA was visualized in prostate cancer tissue microarrays using immunofluorescence (IF) (FIG. 1, panels D-G). Total uPA protein was detected in low and high grade adenocarcinomas and in osseous metastases with IF. Consistent with previous findings, uPA was located in both the epithelium and stroma (Usher et al. (2005) *Int J Cancer* 113, 870-880).

Example 2

U33 Fab Identification and Development

A human naïve B cell phage display library with a diversity of $4.1 \times 10^{10}$ was used to identify inhibitory antibodies against human uPA. After four rounds of panning, 192 independent clones were screened by ELISA. Of these clones, 67 showed high ELISA signals and 23 had unique sequences. The 23 unique clones identified were expressed, purified, and tested for uPA inhibition. uPA inhibition was tested using Spectrozyme® uPA chromogenic substrate (American Diagnostica).

Figure 2:
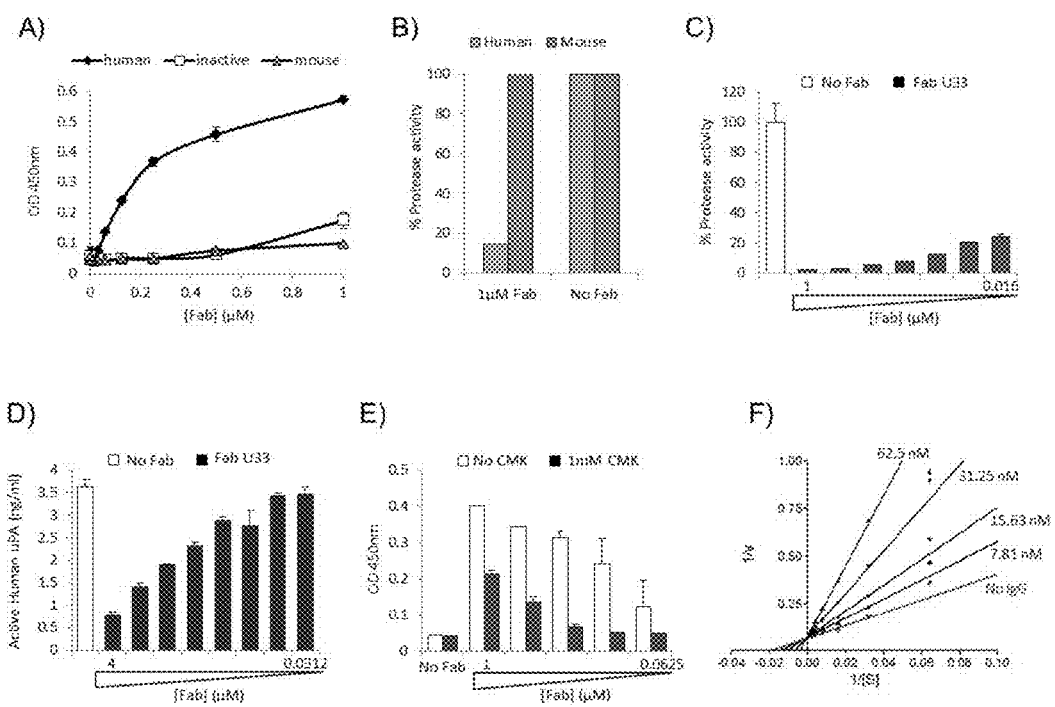
FIG. 2, panel A shows specific binding of the U33 Fab to the active form of uPA. Serial dilutions of pure U33 were added to uPA coated plates and incubated for 1 hour. The amount of Fab bound to uPA was determined by ELISA. U33 Fab was detected only in wells coated with human active uPA. Panel B depicts inhibition of human uPA by U33. The proteolytic activity of human or mouse uPA was read in absence and presence of 1 µM of U33. The enzyme activity is expressed as percentage of the uPA activity in absence of Fab (100%). Panel C shows inhibition of uPA bound to uPAR. Serial dilutions of U33-Fab were added to uPAR-uPA coated plates and incubated for 1 hour and the activity of uPA was read. Panel D depicts prevention of uPA binding to PAI-1 coated plates by U33. Serial dilutions of pure U33 (4 μM to 31.2 nM) were pre-incubated overnight with uPA and added to PAI-1 coated plates. The amount of uPA bound to PAI was determined by ELISA. Panel E shows that U33 does not bind to uPA inhibited by a CMK inhibitor. Serial dilutions of U33 were added to a uPA-coated plate pre-incubated with and without 1 μM CMK. The amount of U33 Fab bound to uPA was determined by ELISA. Panel F shows a Lineweaver-Burk plot demonstrating that U33 IgG is a competitive inhibitor of uPA.

Clone U33 was identified as a Fab that exhibited inhibitory activity. U33 had a Complementarity Determining Region H3 (CDRH3) of 7 amino acids, shorter than the CDRH3 of other inhibitory antibodies of serine proteases described in Schneider et al. (2012) *J Mol Biol* 415:699-715. The affinity and specificity of the U33 Fab was determined using quantitative ELISA as well as inhibition assays with human uPA (active and zymogen) and mouse uPA. ELISA results showed that U33 bound to active uPA in a concentration-dependent manner, but not zymogen uPA or mouse uPA (FIG. 2, panel A). The inhibition data in FIG. 2 (panel B) indicates that U33 Fab inhibits more than 80% of human uPA activity and has no effect on the mouse enzyme.

Under steady-state conditions U33 Fab possessed a $K_i$ of 20 nM for soluble uPA. It has been reported that the enzymatic activity of uPA bound to uPAR is considerably increased compared with the soluble protein. U33 Fab was tested for its ability to inhibit uPAR-bound uPA using plates coated with the uPAR-uPA complex (FIG. 2, panel C). Under these conditions, U33 Fab appeared to be a more potent inhibitor of receptor-bound uPA than of soluble uPA. U33 Fab also blocked binding of uPA to its endogenous inhibitor PAI-1 in a dose dependent manner (FIG. 2, panel D). The binding of U33 Fab to uPA pre-incubated with PAI-1 was also tested, and U33 Fab was found to not disrupt the uPA-PAI-1 complex. U33 Fab was tested to see if it could inhibit active uPA pre-treated with the irreversible active site inhibitor Glu-Gly-Arg-chloromethyl ketone (CMK). When added to the uPA-CMK complex, the binding of U33 Fab to uPA was significantly decreased (FIG. 2, panel E). In contrast, CMK did not inhibit binding of other anti-uPA Fabs obtained during the screen to uPA. The conversion of U33 Fab to the full length IgG decreased the $K_i$ to 10 nM. Kinetic analysis using double reciprocal plots revealed that U33 IgG was a competitive inhibitor of uPA (FIG. 2, panel F). Additionally, U33 IgG was able to displace the non-covalent small molecule inhibitor p-aminobenzamidine in the active site of uPA when incubated with inhibited protease.

Example 3

Characterization of U33 I2G In Vitro

Figure 3:
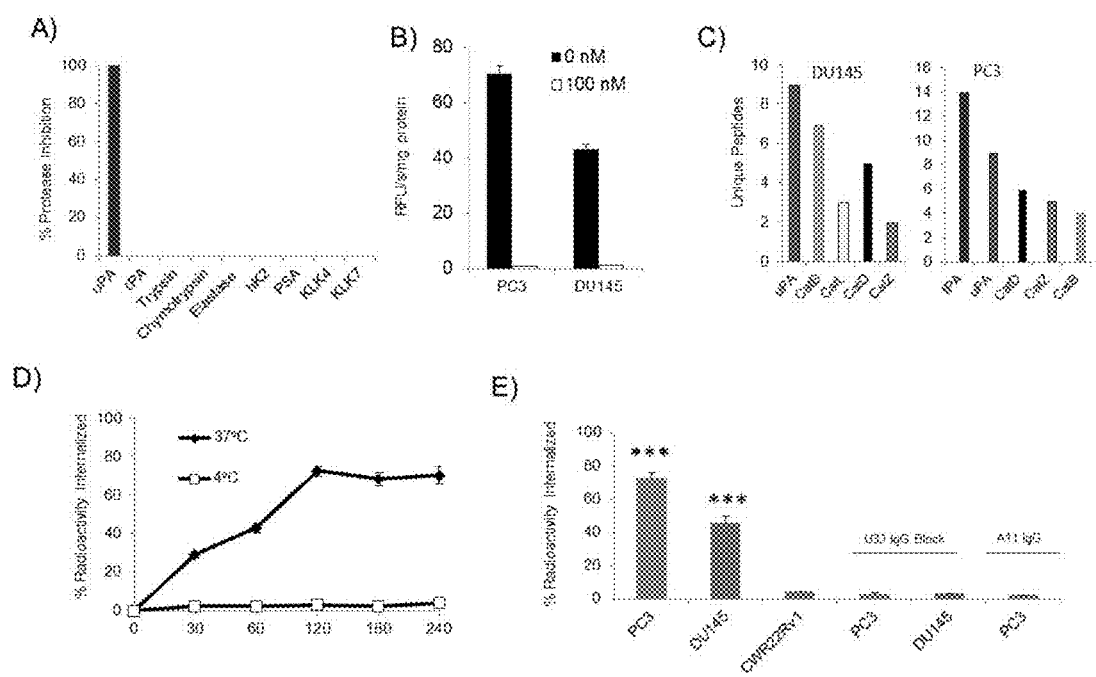
FIG. 3, panel A shows the specificity of U33-IgG for uPA compared to a panel of proteases. Proteases were treated with 1 μM of U33 IgG in the presence of fluorogenic substrate. Panel B depicts inhibition of trypsin-like proteolytic activity in the conditioned media of PC3 and DU145 cells by U33 IgG. Conditioned media were incubated with the trypsin cleavable fluorogenic substrate Z-Gly-Gly-Arg-AMC (ex. 355 nm; em. 460 nm) at 400 μM in the presence and absence of U33 IgG. Panel C shows mass spectrometry proteomic analysis of proteases in the conditioned media from PC3 and DU145 cells. Panel D depicts PC3 cellular internalization of $^{111}$In-U33 IgG at 37° C. and 4° C. in conditioned media. PC3 cells were incubated with 50 nM of radiolabeled antibody at the indicated time points and were washed and treated with an acidic buffer to remove non-covalently bound and non-internalized $^{111}$In-U33 IgG. Each time point was performed in triplicate. Panel E shows internalization of $^{111}$In-U33 IgG at the 120 min time point by the cells lines PC3, DU145 and CWR22Rv1 in conditioned media. Blocking was performed by adding 100 μg of cold U33 IgG to the media prior to addition of radiolabeled antibody. $^{111}$In-A11 IgG was used as the isotype control antibody for the PC3 cells.

U33 IgG was specific for uPA when assayed against a panel of proteases. No cross reactivity was observed with proteases displaying an array of specificities, including the prostate cancer-associated serine proteases hK2, PSA and KLK4 (FIG. 3, panel A). U33 IgG was tested for its ability to inhibit trypsin-like proteolysis in PC3 and DU145 conditioned media (FIG. 3, panel B). When incubated with the generic trypsin fluorogenic substrate, Z-Gly-Gly-Arg-AMC, PC3 and DU145 conditioned media showed substantial trypsin-like activity. Addition of 100 nM U33 IgG inhibited all trypsin-like proteolytic activity. Proteomic analysis of the secreted proteases in the conditioned media found that both cells lines had high levels of uPA. In PC3 conditioned media, tPA was abundant. However, the requirement of fibrin to be active eliminated tPA as a source of trypsin-like proteolytic activity Ke et al. (1997) *J Biol Chem* 272:16603-16609. The other proteases identified in the conditioned media were cathepsins that either did not display activity against the substrate or were not active at physiologic pH.

U33 IgG labeled with $^{111}$In via a DOTA chelate ($^{111}$In-U33 IgG) was internalized by PC3 cells at 37° C. with 72% of the total radioactivity internalized within 120 minutes. A subsequent internalization study conducted at the 120 minute time point found that $^{111}$In-U33 IgG was selectively internalized by cell lines expressing active uPA. Internalization was observed in DU145 cells, but was blocked in PC3 and DU145 cells pre-treated with excess cold U33 IgG.

No internalization occurred in CWR22Rv1 cells and in PC3 cells treated with the isotype control.

Figure 13:
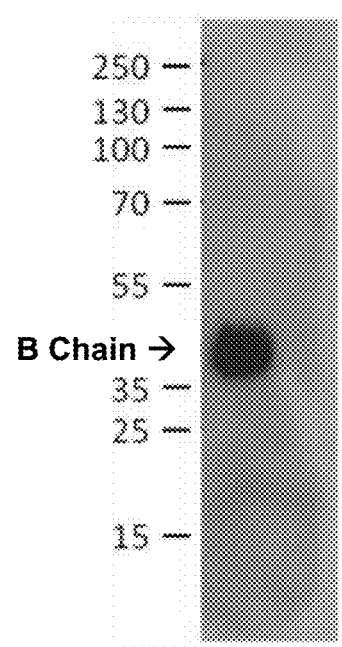
FIG. 13 depicts U33/uPA western-blot analysis under reducing conditions, indicating that U33 specifically recognizes the B-chain of uPA.

Western analysis under reducing conditions was performed to determine which chain of two-chain uPA (the A chain or the B chain) is specifically recognized by U33. 1 µg of recombinant human uPA (R&D Systems) was run in a SDS/PAGE gel using reducing conditions and transferred to a PVDF membrane. The membrane was blocked and incubated with the Fab U33 (1 µg/mL) for 2 hours. The U33 Fab was detected using an anti-myc antibody conjugated to peroxidase. Under reducing conditions, the two chains of active human uPA run separated: B chain (approx. 34 kD) and A chain (approx. 20 kD). The results, shown in FIG. 13, indicate that U33 specifically recognizes the catalytic domain (B chain) of uPA.

ELISA assays were performed to further assess the selectivity of U33 IgG for uPA compared to highly related serine proteases. All proteases were active site-titrated to ensure that identical concentrations of active protease were adsorbed to the ELISA plate. After blocking, increasing concentrations of U33 IgG were incubated for 1 hour at RT. Unbound U33 IgG was removed by washing and bound U33 IgG was detected with an anti-human Fc-HRP secondary. 50 µL of 2.8 nM active protease in coating buffer were added to each well in a Nunc Maxisorb ELISA plate and incubated O/N at 4° C. Unbound protease was removed by hand washing wells 3× with wash buffer. Wells were incubated in 200 µL of Block Solution per well for 2 h at RT. Block Solution was removed by hand washing wells 3× with wash buffer. 50 µL of U33 IgG in Block Solution was added for 1 h at RT. The highest U33 IgG concentration was 651 nM, and was decreased in two-fold increments to 5.1 nM. Unbound U33 IgG was removed by hand washing wells 6× with wash buffer. 50 µL of 1:2000 dilution of secondary antibody in Block Solution was added for 1 h at RT. Unbound secondary antibody was removed by hand washing wells 6× with wash buffer. 100 µL of 1-step Ultra TMB-ELISA was added and then quenched with 100 µL of 1 M HCl. Signal was quantified by measuring $A_{450}$ on plate reader. Results for U33 binding to uPA, thrombin, HGFA, hepsin, chymotrypsin and trypsin are shown in FIG. 4, panel A. Results for U33 binding to uPA, MT-SP1 and plasmin are shown in FIG. 4, panel B. Results for U33 binding to uPA and tPA are shown in FIG. 4, panel C. Results for U33 binding to human uPA and mouse uPA are shown in FIG. 4, panel D. The ELISA data show that at concentrations where U33 IgG saturates uPA, there is no detectable binding to highly related serine proteases that include thrombin, HGFA, hepsin, chymotrypsin, trypsin, MT-SP1, plasmin, tPA, and mouse uPA. Therefore U33 IgG can discriminate between proteases with identical catalytic mechanisms and similar protein folds.

uPA is found in at least four different forms in vivo that include inactive zymogen, active soluble uPA, active uPA bound to uPAR, and PAI-1 inhibited uPA. An ELISA assay was used to determine the selectivity of U33 IgG for these four different species. ELISA assays were performed to further assess the selectivity of U33 IgG for active uPA versus inactive uPA. With the following exceptions, the protocol described in the previous section was utilized: human pro-uPA is inactive, therefore a MUGB titration was not performed. The protein concentration provided by American Diagnostica was used to prepare a 2.8 nM solution of pro-uPA in PBS. Results are shown in FIG. 5, panel A.

To assess binding of U33 to uPA versus uPA complexed to uPAR, either 50 µL of 2.8 nM active uPA OR 50 µL of 2.8 nM uPAR in coating buffer was added to each well in a Nunc Maxisorb ELISA plate and incubated O/N at 4° C. Unbound protein was removed by hand washing wells 3× with wash buffer. Wells were incubated in 200 µL of Block Solution per well for 2 h at RT. Block Solution was removed by hand washing wells 3× with wash buffer. 50 µL of 2.8 nM active uPA was added to uPAR coated wells and incubated at RT for 1 h. Unbound protein was removed by hand washing wells 3× with wash buffer. 50 µL of U33 IgG in Block Solution was added for 1 h at RT. The highest U33 IgG concentration was 651 nM, and was decreased in two-fold increments to 5.1 nM. All subsequent steps are identical to the previously described protocol. Results are shown in FIG. 5, panel B.

To assess binding of U33 to uPA versus uPA inhibited by PAI-1, active uPA was coated to an ELISA plate and wells were blocked as previously described. 50 µL of PAI-1 in Block Solution was added for 1 h at RT. The highest PAI-1 concentration was 133 nM, and was decreased in two-fold increments to 8.3 nM. Unbound protein was removed by hand washing wells 3× with wash buffer. 50 µL of U33 IgG in Block Solution was added for 1 h at RT. The highest U33 IgG concentration was 651 nM, and was decreased in two-fold increments to 5.1 nM. All subsequent steps are identical to the previously described protocol. Results are shown in FIG. 5, panel C.

The above data show that U33 IgG selectively binds to all active forms of uPA but not inactive forms. Accordingly, U33 IgG is useful, e.g., as an activity-based probe.

To determine whether U33 IgG binding was dependent on an accessible active site, uPA was pre-treated with active site-directed inhibitors before U33 IgG addition. In one experiment, uPA was pre-treated with increasing concentration of H-Glu-Gly-Arg-CMK, a tripeptide chloromethylketone inhibitor that binds in the S3 to S1 pockets of uPA and forms a covalent bond with catalytic residues. U33 IgG binding was assessed by ELISA. In another experiment, uPA was pre-treated with p-aminobenzamidine, a non-covalent inhibitor that binds in the S1 pocket of uPA and undergoes a change in fluorescence upon displacement. p-Aminobenzamidine displacement was measured by comparing fluorescent spectra before and after U33 IgG addition.

To assess U33 binding to uPA versus uPA-CMK, active uPA was coated to an ELISA plate and wells were blocked as previously described. 50 µL of H-Glu-Gly-Arg-CMK in Block Solution was added for 1 h at RT. The highest CMK concentration was 7.5 mM, and was decreased in two-fold increments to 467 µM. Unbound protein was removed by hand washing wells 3× with wash buffer. 50 µL of U33 IgG in Block Solution was added for 1 h at RT. The highest U33 IgG concentration was 651 nM, and was decreased in two-fold increments to 5.1 nM. All subsequent steps are identical to previously described protocol. Results are shown in FIG. 6, panel A.

To determine whether U33 could displace p-aminobenzamidine, stocks of uPA and p-aminobenzamidine were prepared in 1×TBST+Ca+2. Equal volumes of 100-µM p-aminobenzamidine and 2 µM uPA or buffer were combined and incubated at room temperature for 1 hour. 50 µL of the p-aminobenzamidine/uPA complex or 50 µL of p-aminobenzamidine alone was added per well to a blacked-walled 96 well plate. 50 µL of 12 µM U33 IgG or 50 µL of 1×TBST+$Ca^{+2}$ was added to wells containing the p-aminobenzamidine/uPA complex or p-aminobenzamidine alone. The final concentrations are 25-µM p-aminobenzamidine, 500-nM uPA, and 6-µM U33 IgG. Fluorescence intensity measurements were made on a Tecan plate reader using an excitation wavelength of 325 nM and collecting emission data from 356 nm-450 nm. Results are shown in FIG. 6, panel B.

The above active site binding studies indicate that U33 IgG can compete with active site directed small molecule inhibitors for uPA binding. The data support that U33 IgG restricts access to the 51 pocket within the uPA active site.

Example 4

U33 IgG In Vivo Imaging

Figure 7:
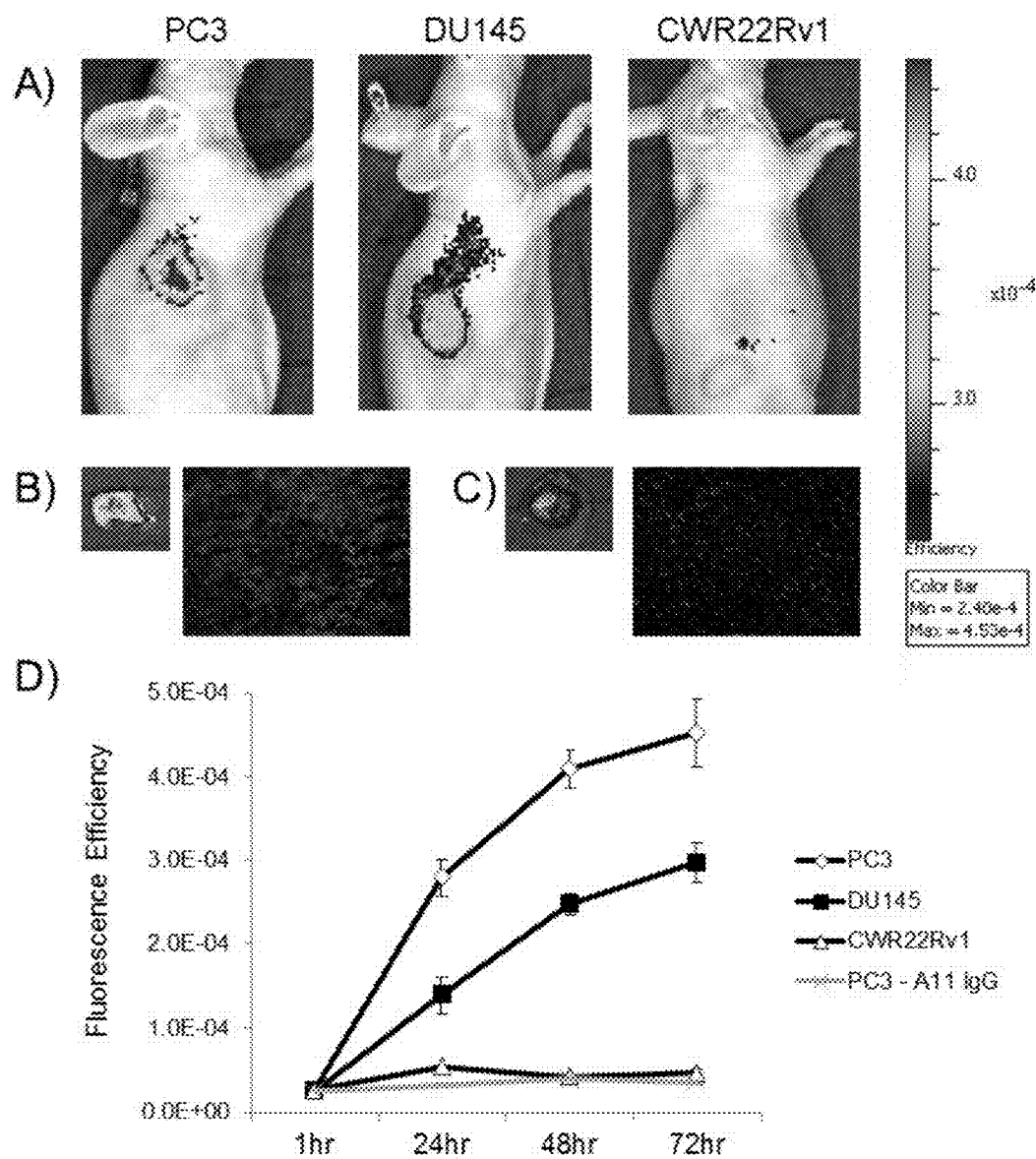
FIG. 7, panels A-D, show near-infrared (NIR) optical imaging of prostate cancer xenografts using AF680-U33 IgG. In panel A, mice bearing PC3, DU145 and CWR22Rv1 xenografts were tail-vein injected with 2 nmol of AF680-U33 IgG and imaged using NIR optical imaging. The images shown are representative of n=3 mice/xenograft and were acquired 72 hrs post-injection. Panel B shows the resected PC3 tumor at 72 hrs fluoresence intensity (left) and a tumor section demonstrating probe penetration and localization by fluoresence microscopy (right). Panel C depicts probe fluoresence intensity (left) and localization (right) in the liver of a PC3 xenograft mouse. Panel D shows a graph depicting the localization of AF680-U33 IgG as fluorescence efficiency of the tumor ROIs for the mice imaged using NIR optical imaging. Included in the graph are the data for the mice imaged with the isotype control AF680-A11 IgG in PC3 xenografts.

U33 IgG was tested for its ability to detect active uPA in vivo using near-infrared (NIR) optical imaging. U33 IgG labeled with AlexaFluor 680 (AF680-U33 IgG) allowed for the qualitative detection of active uPA in xenografts (FIG. 7, panel A). Maximum probe localization was achieved at 72 hrs with the PC3 xenograft demonstrating high tumor uptake and retention. Less tumor uptake was observed in the DU145 xenograft in accordance with the mRNA and MC results. No probe localization was present in the CWR22Rv1 xenograft. Cryosectioning of the PC3 tumor at 72 hrs, and subsequent imaging of AF680-U33 IgG with fluorescence microscopy, found probe penetration in the tumor tissue (FIG. 7, panel B). The accumulation of the probe in the tumor was greater than in the liver, the main clearance organ for IgG antibodies (FIG. 7, panel C). Graphing the fluorescence efficiency of the ROIs for each of the mice imaged as a function of time highlighted the uptake kinetics and selectivity of the probe.

Figure 8:
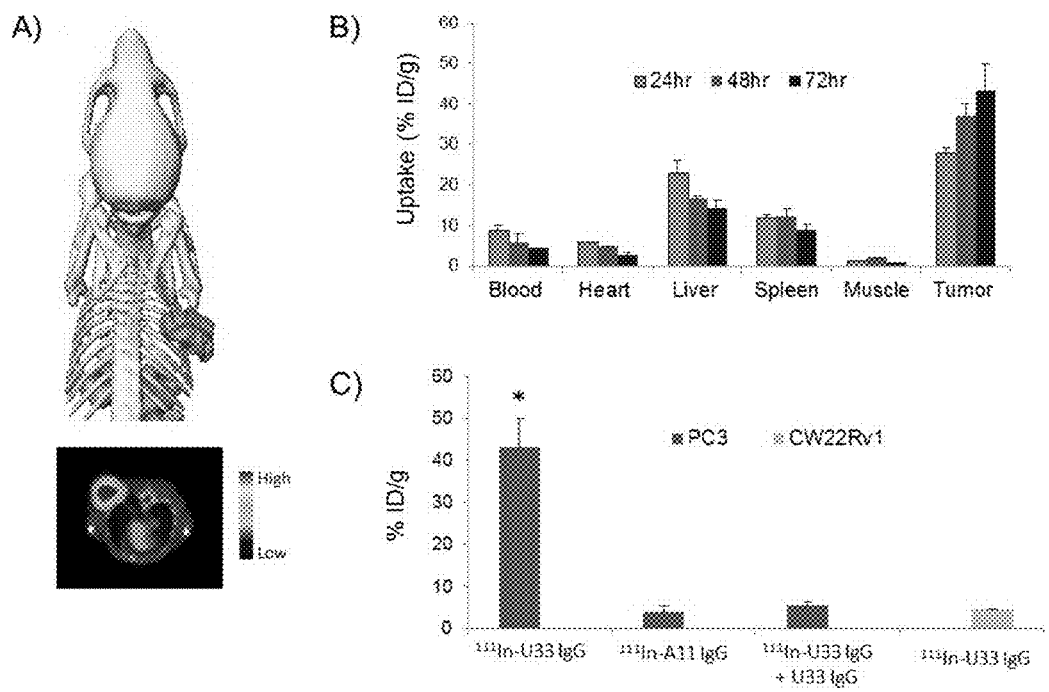
FIG. 8, panels A-C, depict SPECT/CT imaging and biodistribution of $^{111}$In-U33 IgG in xenograft bearing mice. Panel A shows SPECT imaging with $^{111}$In-U33 IgG in a PC3 xenograft model. Depicted are SPECT/CT images shown as a three-dimensional volume rendering of the SPECT data (blue) overlaid onto surface rendered CT data and a reconstructed transverse view using a rainbow color scale to show uptake (below). Imaging is representative of n=3 mice imaged with $^{111}$In-U33 IgG at 72 hrs post-injection. Each animal for imaging received 2.5 μg of antibody corresponding to 220 μCi of activity. As shown in panel B, probe biodistribution was determined by radioactivity assays in PC3 tumor bearing mice (n=4 for each time point). Tissues were harvested at 24, 48 and 72 hrs after injection of $^{111}$In-U33 IgG (25 μCi). Probe uptake is reported as percent injected dose per gram (% ID/g). For each tissue type, the left bar, middle bar, and right bar correspond to 24 hrs, 48 hrs and 72 hrs, respectively. Panel C depicts tumor uptake specificity measured at 72 hrs post-injection (n=4 mice for each treatment). PC3 xenograft bearing mice were treated with isotype control $^{111}$In-A11 IgG (25 μCi) and $^{111}$In-U33 IgG blocked by i.v. pre-injection of 200 μg of cold U33 IgG. Probe uptake in CWR22Rv1 xenografts is also depicted.

The clinically relevant imaging modality SPECT/CT was next used to acquire three-dimensional tomographic data. $^{111}$In-U33 IgG localization was seen 72 hrs post-injection in the PC3 xenograft as documented by a pronounced tumor signal in the 3D data reconstruction and the 2D transverse view of the fused SPECT/CT image (FIG. 8, panel A). In the SPECT/CT images, noticeable hepatic clearance of the probe was observed with little secondary accumulation in other locations. A biodistribution study of $^{111}$In-U33 IgG in the PC3 xenograft found that the probe accumulated preferentially over time in the tumor with a % ID/g of 43.2% at 72 hrs (FIG. 8, panel B). $^{111}$TH-U33 IgG had low background in vivo with a tumor-to-blood ratio of 9.9 and a tumor-to-muscle ratio of 63. Probe accumulation in the PC3 xenograft was blocked in vivo at 72 hrs by pre-treatment with excess cold U33 IgG prior to radiotracer injection. No uptake of $^{111}$In-U33 IgG was found in the CWR22Rv1 xenograft with a % ID/g of 4.8% representing non-specific tumor localization.

Figure 9:
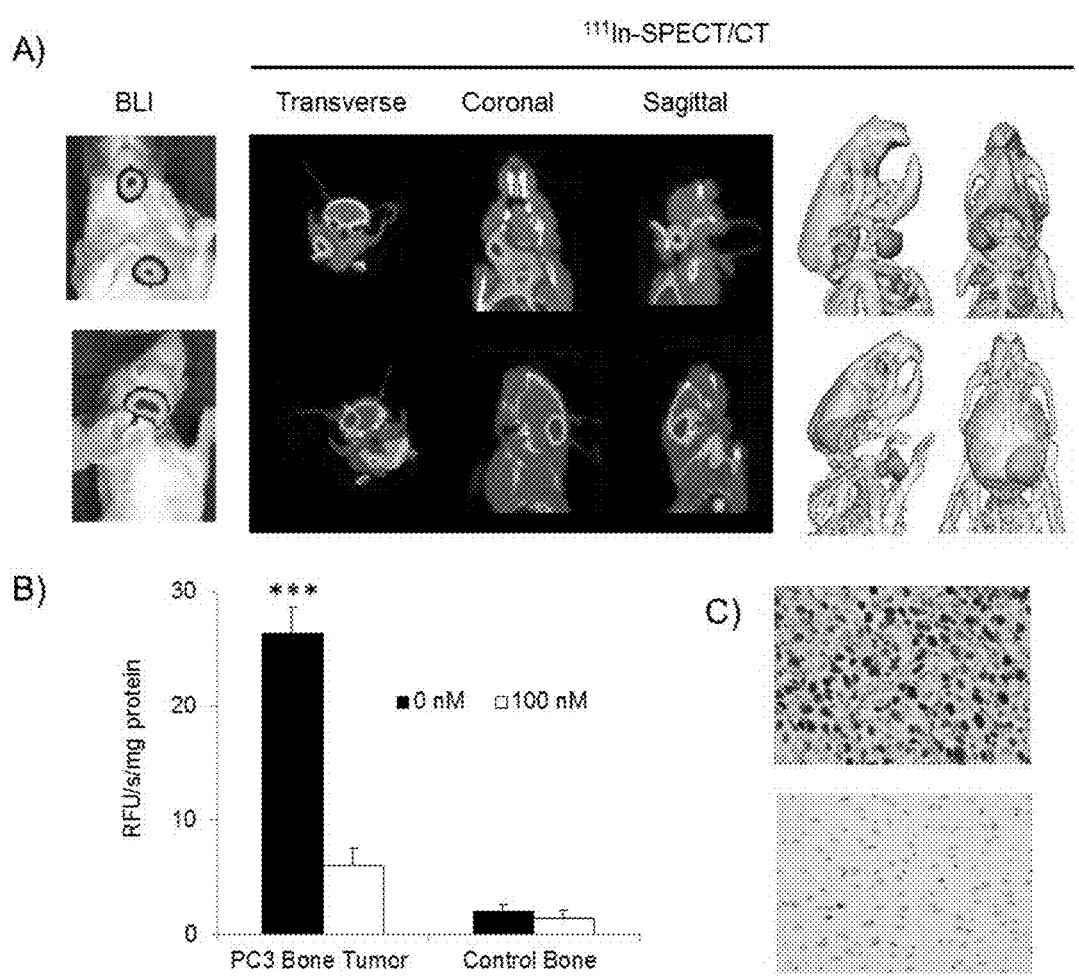
FIG. 9, panels A-C, show imaging of active uPA in the PC3 cardiac dissemination model with 111In-U33 IgG. Panel A depicts 2D and 3D reconstructed $^{111}$In-SPECT/CT images of $^{111}$In-U33 IgG showing co-localization of the metastatic lesions with the bioluminescence imaging (BLI) data. (top) Images showing the localization of the anti-uPA probe to an osseous metastatic lesion in the left mandible of the mouse (top) and probe localization to brain and lymph node metastatic lesions (bottom). Panel B shows inhibition of the trypsin-like proteolytic activity by U33 IgG in the supernatant from the homogenized mandible lesion. Supernatant from homogenate was assayed for proteolytic activity using Z-Gly-Gly-Arg-AMC (400 μM) in the presence and absence of 100 nM U33 IgG. As shown in Panel C, the imaged brain lesion was fixed, sectioned and stained for Ki-67. Intense staining for Ki-67 is apparent in the cancerous lesion (top) compared to normal adjacent brain tissue (bottom).

$^{111}$In-U33 IgG was tested for its ability to detect small dispersed lesions that mimic human prostate cancer using a PC3 intracardiac dissemination model Park et al. (2010) Curr Protoc Pharmacol, Chapter 14, Unit 14-15. The PC3 cells used for this model were engineered to stably express luciferase and the formation of experimental metastatic lesions was monitored by bioluminescence imaging (BLI) after injection of luciferin. By week six, distinct experimental metastases had formed in the bone, brain and lymph nodes of the mice. $^{111}$In-U33 IgG imaged a pronounced osseous lesion in the jaw of this model that was identified by BLI (FIG. 9, panel A). In the 2D and 3D reconstructed views, the lesion (11.6 mm$^3$ volume) was located in the left mandible. The tissue of this lesion was homogenized and the supernatant had marked trypsin-like proteolytic activity, when incubated with the fluorogenic trypsin substrate, compared to normal control tissue extracted from the right mandible (FIG. 9, panel B). This proteolytic activity was significantly inhibited by the addition of 100 nM U33 IgG.

In another example, $^{111}$In-U33 IgG was able to resolve a brain lesion (28.3 mm$^3$ volume) identified by BLI (FIG. 9, panel A). Staining of the brain lession for Ki-67 found that the lesion was highly proliferative compared to adjacent normal tissue (FIG. 9, panels C and D). In addition to the brain lesion, the 2D and 3D reconstructed views also showed the detection of lymph node lesions that were obscured by the intense signal coming from the brain lesion (FIG. 9, panel C).

Figure 10:
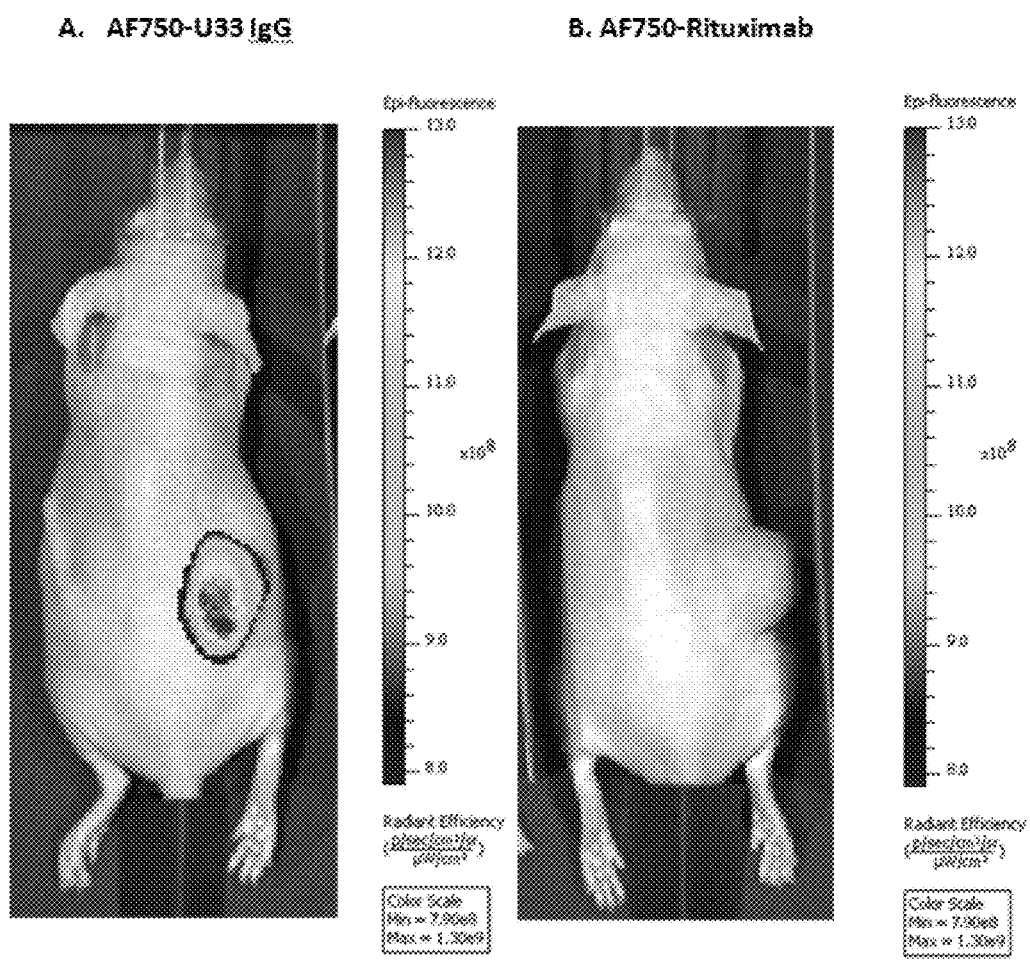
FIG. 10, panels A-B, show in vivo imaging of U33 IgG antibody (panel A) and Rituximab control (panel B) in the human oral squamous cell carcinoma SAS xenograft tumor model.

In vivo imaging of U33 IgG antibody was performed in the human oral squamous cell carcinoma SAS xenograft tumor model. A 10-mg/kg dose of either AF750 labeled U33 IgG or AF750 labeled Rituximab was administered to tumor bearing mice and images taken 72 h after administration using a method similar to that described in the previous examples. Rituximab serves as a control for passive (i.e. antigen independent) accumulation of labeled antibody. SAS tumors do not express Rituximab's target antigen, CD20, and Rituximab does not cross react with mouse CD20. In vivo imaging data is presented in FIG. 10 and shows greater accumulation of U33 IgG (panel A) in SAS tumors than the Rituximab control (panel B). These data suggest that U33 accumulation is due to antigen-dependent binding in the tumor, i.e., the presence of active uPA.

A novel imaging technology for the non-invasive nuclear imaging of aggressive cancer (e.g., prostate cancer) is described above. The development of the SPECT imaging probe, U33 IgG, is documented from its initial discovery, using a human antibody identified from a Fab phage display library, to its evaluation in vivo in prostate cancer models. Targeting the active form of the secreted serine protease uPA, U33 IgG is the first example of a clinically applicable cancer diagnostic that acts by selectively inhibiting a functional enzyme secreted by cancer cells. In healthy prostate tissue, the uPA promoter is epigenetically silenced by hypermethylation resulting in no detectable uPA in the prostate (Shukeir et al. (2006) Cancer Res 66:9202-9210; Pakneshan et al. (2003) FASEB J 17:1081-1088). As prostate cancer progresses, methylation patterns change and uPA is expressed (Pakneshan et al. (2005) Curr Cancer Drug Targets 5:471-488; Nelson et al. (2009) Endocrinology 150:3991-4002). uPA expression is epigenetically regulated and is present regardless of AR status, making it an imaging biomarker for monitoring response to anti-androgens, novel therapies, and for patient stratification. uPA expression was high in the metastatic cells lines PC3 and DU145 and expression was significantly increased in PC3 cells under hypoxia. Although only two clonal derived cell lines expressed uPA, immunofluorescence data found total uPA expression was present in prostate tumors of every grade and in both soft tissue and osseous metastases. These data support and further validate earlier findings attesting to the ubiquitous nature of uPA in prostate cancer.

The development of uPA inhibitors has mainly focused on low molecular weight compounds. The further translation of these molecules has been prevented by poor specificity and off-target effects. A previous attempt to develop an inhibitory antibody for uPA gave a human monoclonal clonal antibody with a low nanomolar affinity (Sgier et al. (2010) Protein Eng Des Sel 23:261-269). This antibody could not, however, distinguish between active uPA and pro-uPA and lacked species specificity. Studies with U33 Fab found the antibody could inhibit both secreted and uPAR bound uPA in the low nanomolar range and was specific for the active human form. U33 Fab could not bind to uPA inhibited by PAI-1 or displace PAI-1 from the complex. Inhibition studies against other proteases, including S1A proteases associated with prostate cancer, found U33 IgG to be a specific, competitive inhibitor of uPA. Further evidence for U33 binding to the active site was provided by use of active site-directed uPA inhibitors. U33 IgG could displace a non-covalent small-molecule inhibitor from the S1 pocket of uPA and pre-incubation of uPA with a covalent CMK inhibitor blocked U33 binding. Based on these data, the present inventors have demonstrated unequivocally that U33 specifically targets active uPA in vitro and in vivo with an accuracy not seen with other activity-based probes.

The imaging properties of U33 IgG in vivo were characteristic of antibody imaging probes that target membrane proteins. Although targeting a secreted protein, U33 IgG demonstrated high tumor uptake and retention in uPA-expressing xenografts by NIR and SPECT imaging. U33 IgG was sensitive enough to detect small osseous and soft tissue metastatic lesions a few millimeters in size using SPECT/CT. Key to the success of U33 IgG as an imaging probe was its internalization. This occurred via a time-dependent endocytic pathway in PC3 and DU145 cells, but not in PA negative CWR22Rv1. Internalization was blocked with excess cold U33 IgG suggesting that internalization was due to a mechanism requiring the presence of active uPA. Since both cell lines also express uPAR, it appears that internalization is meadiated by uPAR with U33 IgG acting the role of PAI-1. Both PAI-1 and U33 IgG bind to the N-terminal domain of uPA, while uPAR binding occurs at the C-terminal protease domain. In vivo, this novel internalization mechanism afforded probe accumulation and sequestration of the uPA-U33 IgG complex in tumor tissue. Internalization prevented the dissemination of the uPA-U33 IgG complex to peripheral tissue resulting in high tumor uptake values that increased over time as demonstrated by the biodistribution. The internalization of U33 IgG is in direct contrast to reports that targeted another secreted protease, prostate-specific antigen (PSA), for PET imaging using a murine IgG antibody ($^{89}$Zr-5A10) (Ulmert et al. (2012) *Cancer Discov* 2:320-327). With no means of internalization or bioaccumulation, $^{89}$Zr-5A10 uptake reached its zenith 24 hrs post-injection with a low tumor-to-blood ratio.

The above data demonstrates that U33 is a novel, highly potent and selective active site inhibitor of uPA that can be used to non-invasively image uPA related cancers (e.g., prostate cancer). Notably, the utility of U33 IgG is not limited to prostate cancer. uPA and the other components of the PAS are over-expressed and known to contribute to the progress of a myriad of cancers (Dass et al. (2008) *Cancer Treat Rev* 34:122-136). U33 IgG has the potential to be both a diagnostic and therapeutic agent. The internalization and clearance from the blood makes U33 IgG an ideal candidate for delivering therapeutic payloads as a drug conjugate or for radioimmunotherapy with beta and alpha emitting radionuclides. In summary, the platform technology described here has the immediate potential to change the way cancer is treated, imaged, and/or the like, leading to better therapeutic options and prolonged patient survival.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An antibody, or antigen-binding fragment thereof, comprising:
   a heavy chain complementary determining region 1 (HCDR1) having the amino acid sequence of SEQ ID NO: 1;
   a heavy chain complementary determining region 2 (HCDR2) having the amino acid sequence of SEQ ID NO: 2;
   a heavy chain complementary determining region 3 (HCDR3) having the amino acid sequence of SEQ ID NO: 3;
   a light chain complementary determining region 1 (LCDR1) having the amino acid sequence of SEQ ID NO: 4;
   a light chain complementary determining region 2 (LCDR2) having the amino acid sequence of SEQ ID NO: 5; and
   a light chain complementary determining region 3 (LCDR3) having the amino acid sequence of SEQ ID NO: 6.

2. The antibody, or antigen-binding fragment thereof, according to claim 1 comprising:
   a light chain variable region comprising a polypeptide having at least 95% amino acid identity to the variable region of SEQ ID NO: 8; and
   a heavy chain variable region comprising a polypeptide having at least 95% amino acid identity to the variable region of SEQ ID NO: 7.

3. The antibody, or antigen-binding fragment thereof, according to claim 1 comprising:
   a light chain comprising a polypeptide having at least 95% amino acid identity to SEQ ID NO: 8; and
   a heavy chain comprising a polypeptide having at least 95% amino acid identity to SEQ ID NO: 7.

4. The antibody, or antigen-binding fragment thereof, according to claim 1, wherein the antibody or antigen-binding fragment thereof is selected from the group consisting of: an IgG, Fv, scFv, Fab, F(ab')2, or Fab'.

5. An antibody, or antigen-binding fragment thereof, that specifically binds urokinase-type plasminogen activator (uPA) comprising:

a light chain variable region comprising a polypeptide having at least 95% amino acid identity to the variable region of SEQ ID NO: 8; and a heavy chain variable region comprising a polypeptide having at least 95% amino acid identity to the variable region of SEQ ID NO: 7.

6. The antibody, or antigen-binding fragment thereof, according to claim 5 comprising:

a light chain comprising a polypeptide having at least 95% amino acid identity to SEQ ID NO: 8; and a heavy chain comprising a polypeptide having at least 95% amino acid identity to SEQ ID NO: 7.

7. A conjugate comprising:

an antibody, or antigen-binding fragment thereof, according to claim 5; and an agent selected from the group consisting of: a therapeutic agent, and a labeling agent.

8. The conjugate of claim 7, wherein the agent is a therapeutic agent.

9. The conjugate of claim 8, wherein the therapeutic agent is a cytotoxic agent selected from the group consisting of: a radionuclide, a chemotherapeutic agent, and a toxin.

10. The conjugate of claim 7, wherein the agent is a labeling agent.

11. The conjugate of claim 10, wherein the labeling agent is an in vivo imaging agent.

12. A pharmaceutical composition comprising:

an antibody or antigen-binding fragment thereof according to claim 1; and a pharmaceutically acceptable carrier.

13. The composition according to claim 12 comprising an agent selected from the group consisting of: a therapeutic agent, and a labeling agent.

14. The composition according to claim 13, wherein the agent is a therapeutic agent.

15. The composition according to claim 14, wherein the therapeutic agent is a cytotoxic agent selected from the group consisting of: a radionuclide, a chemotherapeutic agent, and a toxin.

16. The antibody, or antigen-binding fragment thereof, according to claim 1 comprising:

a light chain variable region comprising a polypeptide having the amino acid sequence of the variable region of SEQ ID NO: 8; and a heavy chain variable region comprising a polypeptide having the amino acid sequence of the variable region of SEQ ID NO: 7.

17. The antibody, or antigen-binding fragment thereof, according to claim 1 comprising:

a light chain comprising a polypeptide having the amino acid sequence of SEQ ID NO: 8; and a heavy chain comprising a polypeptide having the amino acid sequence of SEQ ID NO: 7.

18. A method for treating cancer comprising the step of administering to a subject in need thereof a therapeutically effective amount of an antibody, or antigen-binding fragment thereof, according to claim 5.

19. The method of claim 18, wherein the cancer is selected from the group consisting of: prostate cancer, breast cancer, gastric cancer, colorectal cancer, esophageal cancer, renal cancer, endometrial cancer, and ovarian cancer.

20. The method of claim 18, wherein the cancer is castration-resistant prostate cancer (CRPC).

21. The method of claim 18, wherein the antibody, or antigen-binding fragment thereof, is conjugated to a therapeutic agent.

22. The method according to claim 21, wherein the therapeutic agent is a cytotoxic agent selected from the group consisting of: a radionuclide, a chemotherapeutic agent, and a toxin.

* * * * *

SEQUENCE LISTING

```
<160> NUMBER OF SEQ ID NOS: 11

<210> SEQ ID NO 1
<211> LENGTH: 10
<212> TYPE: PRT
<213> ORGANISM: Homo sapiens

<400> SEQUENCE: 1

Gly Phe Thr Phe Gly Asp Tyr Ala Met Ser
1               5                   10

<210> SEQ ID NO 2
<211> LENGTH: 12
<212> TYPE: PRT
<213> ORGANISM: Homo sapiens

<400> SEQUENCE: 2

Phe Ile Arg Ser Lys Ala Tyr Gly Gly Thr Thr Glu
1               5                   10

<210> SEQ ID NO 3
<211> LENGTH: 7
<212> TYPE: PRT
<213> ORGANISM: Homo sapiens

<400> SEQUENCE: 3

Ile Arg Gly Ala Asn Trp Asn
1               5

<210> SEQ ID NO 4
<211> LENGTH: 16
```

```
<212> TYPE: PRT
<213> ORGANISM: Homo sapiens

<400> SEQUENCE: 4

Arg Ser Ser Gln Thr Leu Met Asn Arg Asn Gly Asn Asn Phe Leu Asp
1               5                   10                  15

<210> SEQ ID NO 5
<211> LENGTH: 7
<212> TYPE: PRT
<213> ORGANISM: Homo sapiens

<400> SEQUENCE: 5

Leu Gly Ser Asn Arg Ala Pro
1               5

<210> SEQ ID NO 6
<211> LENGTH: 9
<212> TYPE: PRT
<213> ORGANISM: Homo sapiens

<400> SEQUENCE: 6

Met Gln Arg Ile Glu Phe Pro Tyr Thr
1               5

<210> SEQ ID NO 7
<211> LENGTH: 244
<212> TYPE: PRT
<213> ORGANISM: Homo sapiens

<400> SEQUENCE: 7

Glu Val Gln Leu Val Gln Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
                20                  25                  30

Ala Met Ser Trp Val Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Ile Arg Gly Ala Asn Trp Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Ala Ala Ala His His His
    210                 215                 220
```

His His His Gly Ala Ala Glu Gln Lys Leu Ile Ser Glu Glu Asp Leu
225                 230                 235                 240

Asn Gly Ala Ala

<210> SEQ ID NO 8
<211> LENGTH: 219
<212> TYPE: PRT
<213> ORGANISM: Homo sapiens

<400> SEQUENCE: 8

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Thr Leu Met Asn Arg
            20                  25                  30

Asn Gly Asn Asn Phe Leu Asp Trp Tyr Leu Gln Lys Pro Gly Gln Ser
        35                  40                  45

Pro Gln Leu Leu Ile Tyr Leu Gly Ser Asn Arg Ala Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Arg
                85                  90                  95

Ile Glu Phe Pro Tyr Thr Phe Gly Gln Gly Thr Lys Leu Glu Ile Lys
            100                 105                 110

Arg Thr Val Val Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 663
<212> TYPE: DNA
<213> ORGANISM: Homo sapiens

<400> SEQUENCE: 9
gaaattgtgc tgactcagtc tccactctcc ctgcccgtca cccctggaga gccggcctcc      60
atctcctgca ggtctagtca gaccctcatg aatagaaatg gaaacaactt tttggattgg     120
tacctgcaga agccagggca gtctccacag ctcctgatct acttgggttc taatcgggcc     180
cccggggtcc ctgacaggtt cagtggcagt ggatcaggca cagattttac actgaaaatc     240
agcagagtgg aggctgagga tgttggggtt tattactgca tgcaacgtat agagtttccg     300
tacacttttg gccaggggac caagctggag atcaaacgaa ctgtggttgc accatctgtc     360
ttcatcttcc cgccatctga tgagcagttg aaatctggaa ctgcctctgt tgtgtgcctg     420
ctgaataact tctatcccag agaggctaaa gtacagtgga aggtggataa cgccctccaa     480

```
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttaa    660
taa                                                                 663
```

```
<210> SEQ ID NO 10
<211> LENGTH: 738
<212> TYPE: DNA
<213> ORGANISM: Homo sapiens

<400> SEQUENCE: 10
gaggtccagc tggtacagtc tgggggaggc ttggtaaagc cagggcggtc cctgagactc     60
tcctgtacag cttctggatt cacctttggt gattatgcta tgagctgggt ccgccaggct    120
ccagggaagg ggctggagtg ggtaggtttc attagaagca aagcttatgg tgggacaaca    180
gaatacgccg cgtctgtgaa aggcagattc accatctcaa gagatgattc caaaagcatc    240
gcctatctgc aaatgaacag cctgaaaacc gaggacacag ccgtgtatta ctgtatcaga    300
ggtgcaaact ggaactgggg ccagggcacc ctggtcaccg tctcaagcgc tccaccaag     360 ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtcca caccttcccg gctgtcctac agtcctcagg actctactcc    540
ctcagcagcg tagtgaccgt gccctccagc agcttgggca cccagaccta catctgcaac    600
gtgaatcaca agcccagcaa caccaaggtg gacaagaaag ttgagcccaa atcttgtgcg    660
gccgcacatc atcatcacca tcacggggcc gcagaacaaa aactcatctc agaagaggat    720
ctgaatgggg ccgcatag                                                  738
```

```
<210> SEQ ID NO 11
<211> LENGTH: 431
<212> TYPE: PRT
<213> ORGANISM: Homo sapiens

<400> SEQUENCE: 11

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
                20                  25                  30

Cys Leu Asn Gly Gly Thr Cys Val Ser Asn Lys Tyr Phe Ser Asn Ile
            35                  40                  45

His Trp Cys Asn Cys Pro Lys Lys Phe Gly Gly Gln His Cys Glu Ile
        50                  55                  60

Asp Lys Ser Lys Thr Cys Tyr Glu Gly Asn Gly His Phe Tyr Arg Gly
65                  70                  75                  80

Lys Ala Ser Thr Asp Thr Met Gly Arg Pro Cys Leu Pro Trp Asn Ser
                85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125

Arg Arg Pro Trp Cys Tyr Val Gln Val Gly Leu Lys Pro Leu Val Gln
    130                 135                 140

Glu Cys Met Val His Asp Cys Ala Asp Gly Lys Lys Pro Ser Ser Pro
```

-continued

```
                145                 150                 155                 160
Pro Glu Glu Leu Lys Phe Gln Cys Gly Gln Lys Thr Leu Arg Pro Arg
                    165                 170                 175

Phe Lys Ile Ile Gly Gly Glu Phe Thr Thr Ile Glu Asn Gln Pro Trp
                    180                 185                 190

Phe Ala Ala Ile Tyr Arg Arg His Arg Gly Gly Ser Val Thr Tyr Val
                    195                 200                 205

Cys Gly Gly Ser Leu Ile Ser Pro Cys Trp Val Ile Ser Ala Thr His
210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                    245                 250                 255

Glu Asn Leu Ile Leu His Lys Asp Tyr Ser Ala Asp Thr Leu Ala His
                    260                 265                 270

His Asn Asp Ile Ala Leu Leu Lys Ile Arg Ser Lys Glu Gly Arg Cys
                    275                 280                 285

Ala Gln Pro Ser Arg Thr Ile Gln Thr Ile Cys Leu Pro Ser Met Tyr
    290                 295                 300

Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
                    325                 330                 335

Val Lys Leu Ile Ser His Arg Glu Cys Gln Gln Pro His Tyr Tyr Gly
                    340                 345                 350

Ser Glu Val Thr Thr Lys Met Leu Cys Ala Ala Asp Pro Gln Trp Lys
            355                 360                 365

Thr Asp Ser Cys Gln Gly Asp Ser Gly Gly Pro Leu Val Cys Ser Leu
                370                 375                 380

Gln Gly Arg Met Thr Leu Thr Gly Ile Val Ser Trp Gly Arg Gly Cys
385                 390                 395                 400

Ala Leu Lys Asp Lys Pro Gly Val Tyr Thr Arg Val Ser His Phe Leu
                    405                 410                 415

Pro Trp Ile Arg Ser His Thr Lys Glu Glu Asn Gly Leu Ala Leu
                    420                 425                 430
```